United States Patent
Murphy et al.

(10) Patent No.: US 11,730,960 B2
(45) Date of Patent: Aug. 22, 2023

(54) ULTRASOUND SYSTEMS AND ASSOCIATED DEVICES AND METHODS FOR MODULATING BRAIN ACTIVITY

(71) Applicant: Attune Neurosciences, Inc., Menlo Park, CA (US)

(72) Inventors: Keith R. Murphy, San Fransico, CA (US); Pablo Villoslada, Los Altos, CA (US); Rajiv Mahadevan, Portola Valley, CA (US)

(73) Assignee: ATTUNE NEUROSCIENCES, INC., Menlo Park, CA (US)

( * ) Notice: Subject to any disclaimer, the term of this patent is extended or adjusted under 35 U.S.C. 154(b) by 0 days.

(21) Appl. No.: 17/332,934

(22) Filed: May 27, 2021

(65) Prior Publication Data

US 2021/0370064 A1    Dec. 2, 2021

Related U.S. Application Data

(60) Provisional application No. 63/030,850, filed on May 27, 2020.

(51) Int. Cl.
*A61N 1/36* (2006.01)
*G06N 20/00* (2019.01)
(Continued)

(52) U.S. Cl.
CPC ....... *A61N 1/36031* (2017.08); *A61N 1/0484* (2013.01); *G06N 20/00* (2019.01); *A61N 2007/0021* (2013.01)

(58) Field of Classification Search
None
See application file for complete search history.

(56) References Cited

U.S. PATENT DOCUMENTS

2014/0058292 A1   2/2014   Alford et al.
2014/0187973 A1*  7/2014   Brown ................ G16H 50/20
                                                      600/483
(Continued)

FOREIGN PATENT DOCUMENTS

WO    WO 2014/116850    *  7/2014

OTHER PUBLICATIONS

Papalambros et al., "Acoustic Enhancement of Sleep Slow Oscillations and Concomitant Memory Impairment in Older Adults", Frontiers in Human Neuroscience, vol. 11, Article 109, Mar. 2017, pp. 1-14. (Year: 2017).*

(Continued)

*Primary Examiner* — Katherine L Fernandez
(74) *Attorney, Agent, or Firm* — Maynard Nexsen PC; Ilya S. Mirov, Esq.

(57) ABSTRACT

The present specification discloses a neuromodulation system comprising a transcranially mounted neuromodulation device and a stimulation control computing environment. The disclosed neuromodulation device comprising at least one ultrasound transducer and at least one EEG electrode and the disclosed stimulation control computing environment comprises a stimulation control unit and offline computing device, the disclosed stimulation control unit including associated systems and methods for controlling the neuromodulation device functionality using acoustic simulations performed on brain image data as well as methods and uses of such neuromodulation systems in modulating brain activity using focused ultrasound stimulation of the thalamus and thalamic sub regions during certain phases of slow wave brain oscillations in order to treat various neural-based disorders or conditions including sleep disorders.

15 Claims, 16 Drawing Sheets

(51) Int. Cl.
*A61N 1/04* (2006.01)
*A61N 7/00* (2006.01)

(56) References Cited

U.S. PATENT DOCUMENTS

| | | |
|---|---|---|
| 2016/0242648 A1* | 8/2016 | Konofagou ............ A61B 3/113 |
| 2018/0014784 A1* | 1/2018 | Heeger ................ A61B 5/6843 |
| 2018/0117364 A1 | 5/2018 | Jordan et al. |
| 2018/0192990 A1* | 7/2018 | Tanter ....................... B06B 3/04 |
| 2019/0105517 A1 | 4/2019 | Tyler |
| 2020/0139113 A1* | 5/2020 | Shin ......................... A61N 5/06 |
| 2020/0188697 A1* | 6/2020 | Kabrams .................. G06N 3/04 |
| 2020/0222699 A1* | 7/2020 | de Zambotti ...... A61N 1/36128 |
| 2021/0170204 A1* | 6/2021 | Vortman ........... A61M 37/0092 |

OTHER PUBLICATIONS

PCT/US2021/034640 International Search Report, dated Sep. 23, 2021.
Gent, Thomas C et al. "Thalamic dual control of sleep and wakefulness." Nature neuroscience vol. 21,7 (2018): 974-984.

\* cited by examiner

ULTRASOUND SYSTEMS AND ASSOCIATED DEVICES AND METHODS FOR MODULATING BRAIN ACTIVITY

This application claims the benefit of priority and is entitled to the filing date pursuant to 35 U.S.C. § 119(e) of U.S. Provisional Patent Application 63/030,850, filed May 27, 2020, the content of which is hereby incorporated by reference in its entirety.

FIELD OF THE INVENTION

The present disclosure generally relates to devices, and associated systems methods, and uses for modulating brain activity using ultrasound stimulation.

BACKGROUND

Sleep is a restorative state in which the brain transiently shifts neural engagement towards internal processes, partially disconnecting the brain from the outside world. Over a century of research has revealed that sleep quality is critical for cognition and overall good health, and that insufficient sleep can have dire consequences. Most apparent are significant reductions in decision making efficiency and accuracy and sensory processing associated with sleep loss. A vast pool of evidence also shows the long-term detriment caused by sleep loss as shown by adverse correlations with motivational state, memory stability, dementia, and Alzheimer's. Beyond conscious action, the detriment of sleep loss extends to physiological health and is linked with countless ailments including Alzheimer's, obesity, immune disorders, and cardiovascular disease. It is estimated that productivity decline from sleep loss costs over $400 Billion annually in the United States alone, not accounting for potential correlates with other costly disease states. Thus, improving the quality of, and the ease of entering sleep represent opportunities to improve both human health and productivity.

Studies have shown that the most restorative period of sleep occurs when the brain enters a state characterized by delta wave or slow wave activity. As such, enhancing slow wave activity represents a major effort to improve sleep quality in diseased and healthy individuals alike. Current therapeutics and methodologies for enhancing slow waves include pharmacological approaches and neuromodulation devices. Pharmacological compounds for slow wave enhancement include $\alpha 2$-$\delta$ calcium channel ligands, serotonin $(5HT)_{2A}$ receptor antagonists, and site promiscuous compounds such as trazodone and others. Various biologically derived compounds have also been identified for use in sleep therapies, such as human growth hormone and prolactin. Although many drugs are partially effective, their benefits are offset by an array of tolerance, efficacy, adherence, and addiction issues which has precluded widespread adoption.

Alternatively, non-invasive closed loop devices have been created to enhance slow waves by delivering stimuli during the "up state" of slow waves. This state is described by the enriched activity of the cortex by thalamic connections during a slow wave and can be seen as the peak positive voltage during a slow wave. In comparison, the "down state" is the period of a slow wave of cortical quiescence. Examples of the stimuli delivered during the up state include transcranial direct current stimulation (tDCS) which drives a small current across superficial layers of the cortex via electrodes on the scalp, auditory stimulation devices in which low intensity audible sounds are played to enhance SWS, or even vestibular stimulation through the swaying of a hammock or cradle. While these devices circumvent tolerance and addiction issues, it is unclear whether their efficacy is comparable to available pharmacological treatments for enhancing SWS. One technical problem associated with current devices is that they operate opportunistically, interfacing with what brain tissue is available from the transcranial surface, rather than targeting desired tissue. Another major drawback of these technologies is their gross lack spatial resolution and specificity for the cortex, or brain sites related to slow wave generation, which likely accounts for the harrowing side effects and/or lack of efficacy.

Thus, what is needed is a non-invasive closed loop device that can modulate slow waves by targeted ultrasonic stimulation of the thalamus.

SUMMARY

The present specification discloses a neuromodulation system comprising a wearable neuromodulation device and a stimulation control computing environment. The disclosed device comprising a wearable device housing or frame including one or more EEG electrodes, one of more ultrasound transducer arrays. The disclosed device can further comprise one or more EEG signal amplifiers and/or a digital analog converter. The disclosed device housing includes a main band having conductive wiring embedded within a core channel of the main band. The disclosed conductive wiring comprising a first conductive wiring and a second conductive wiring. The first conductive wiring connects the one or more EEG electrodes to one or more EEG signal amplifiers, a digital analog converter, and a stimulation control unit before exiting via a port on a back portion of the main band. The EEG electrodes may also have preamplification on the headband, obviating the need for a downstream EEG signal amplifier. The second conductive wiring connects the one of more ultrasound transducer arrays to a stimulation control unit before exiting via the port. In aspects, the disclosed one or more EEG electrodes includes a first front EEG electrode located on a front portion of the main band. Each of the disclosed one or more ultrasound transducer arrays comprise one or more ultrasound-emitting elements. In aspects, the disclosed one or more ultrasound transducer arrays includes a first side ultrasound transducer array located on a first side portion of the main band and a second ultrasound transducer array located on a second side portion of the main band.

A disclosed stimulation control computing environment comprising a stimulation control unit and an offline computing device. A stimulation control unit comprises one or more processors configured to execute algorithms that process real-time information acquired by the one or more EEG electrodes to categorize brain activity. An offline assessment of brain and cranial anatomy using brain imaging or EEG derived predictions provides cranial anatomy to identify and target one or more specific regions of the brain. Offline software calculates phase corrections to individual elements of the ultrasound array to steer the beam to a single, or multiple targets. These phase corrections will be used in real time to target the one or more specific regions of the brain for an ultrasound stimulation and administer the ultrasound stimulation to the one or more specific regions of the brain for a certain period of time.

The present specification also discloses a neuromodulation system comprising a wearable neuromodulation device and a stimulation control computing environment for use in preventing and/or treating a brain disorder. The present specification also discloses methods and uses for preventing and/or treating a brain disorder. Non-limiting aspects of a brain disorder include a sleep disorder, a brain disorder associated with a sleep disturbance, a psychiatric disorder, a metabolic disorder, an epilepsy or other seizure disorder, an anxiety, a depression, and/or a neuropathic pain.

BRIEF DESCRIPTION OF THE DRAWINGS

The accompanying drawings, which are incorporated in and constitute a part of this specification, illustrate aspects of the disclosed subject matter in at least one of its exemplary embodiments, which are further defined in detail in the following description. Features, elements, and aspects of the disclosure are referenced by numerals with like numerals in different drawings representing the same, equivalent, or similar features, elements, or aspects, in accordance with one or more embodiments. The drawings are not necessarily to scale, emphasis instead being placed upon illustrating the principles herein described and provided by exemplary embodiments of the invention. In such drawings:

FIG. 1B showing exemplary hardware components of a neuromodulation device disclosed herein;

FIG. 3B showing a schematic of a system integrating the hardware, online software and offline software aspects in accordance with the teachings of the instant disclosure;

FIG. 4B showing EEG traces of sleep stages collected from an individual revealing the large slow oscillations that appear in N2 NREM and N3 NREM sleep; FIG. 4C showing a color map of slow wave phase relative to "Up" and "Down" states; FIG. 4D showing a phase prediction by sine fitting to EEG slow wave sleep; and FIG. 4E showing a phase prediction by stimulation delivered at phase 0/360°;

FIG. 5B showing image of FIG. 5A taken from a coronal plane showing an image created by MRI scanning with anterior commissure marked as control point (crosshairs) used to compute the maximum angle relative to most posterior and anterior portion of the thalamus; FIG. 5C showing the variation in target angle relative to transducer position on the skull for estimation of beam steering needs; FIG. 5D showing an acoustic simulation of the ultrasound beam onto the image of FIG. 5A when steered at a 20° angle relative to the plane of the transducer; FIG. 5E showing an image created by MRI scan taken from an axial plane illustrating image registration and segmentation of brain regions to identify thalamic region; FIG. 5F showing image of FIG. 5E illustrating electronic element excitation phase being varied to achieve differential focusing in three dimensions to stimulate thalamic region using an exemplary stimulation control unit disclosed herein; FIG. 5G showing electronic element excitation parameters being varied over time to achieve differential focusing; FIG. 5H showing an image created by MRI scan taken from a coronal plane illustrating image registration and segmentation of brain regions to identify thalamic region; FIG. 5I showing image of FIG. 5H illustrating electronic element excitation phase being varied to achieve differential focusing in three dimensions to stimulate thalamic region using an exemplary stimulation control unit disclosed herein; and FIG. 5J showing electronic element excitation parameters being varied over time to achieve differential focusing;

FIG. 7B being a continuation of FIG. 7A and showing a second portion of the control system algorithm;

FIG. 8B being a continuation of FIG. 8A and showing a second portion of the exemplary deep learning network; and FIG. 8C being a continuation of FIG. 8B and showing a third portion of the exemplary deep learning network; FIG. 9B showing a comparison between human annotation and the sleep stage prediction.

DETAILED DESCRIPTION

Figure 1A:
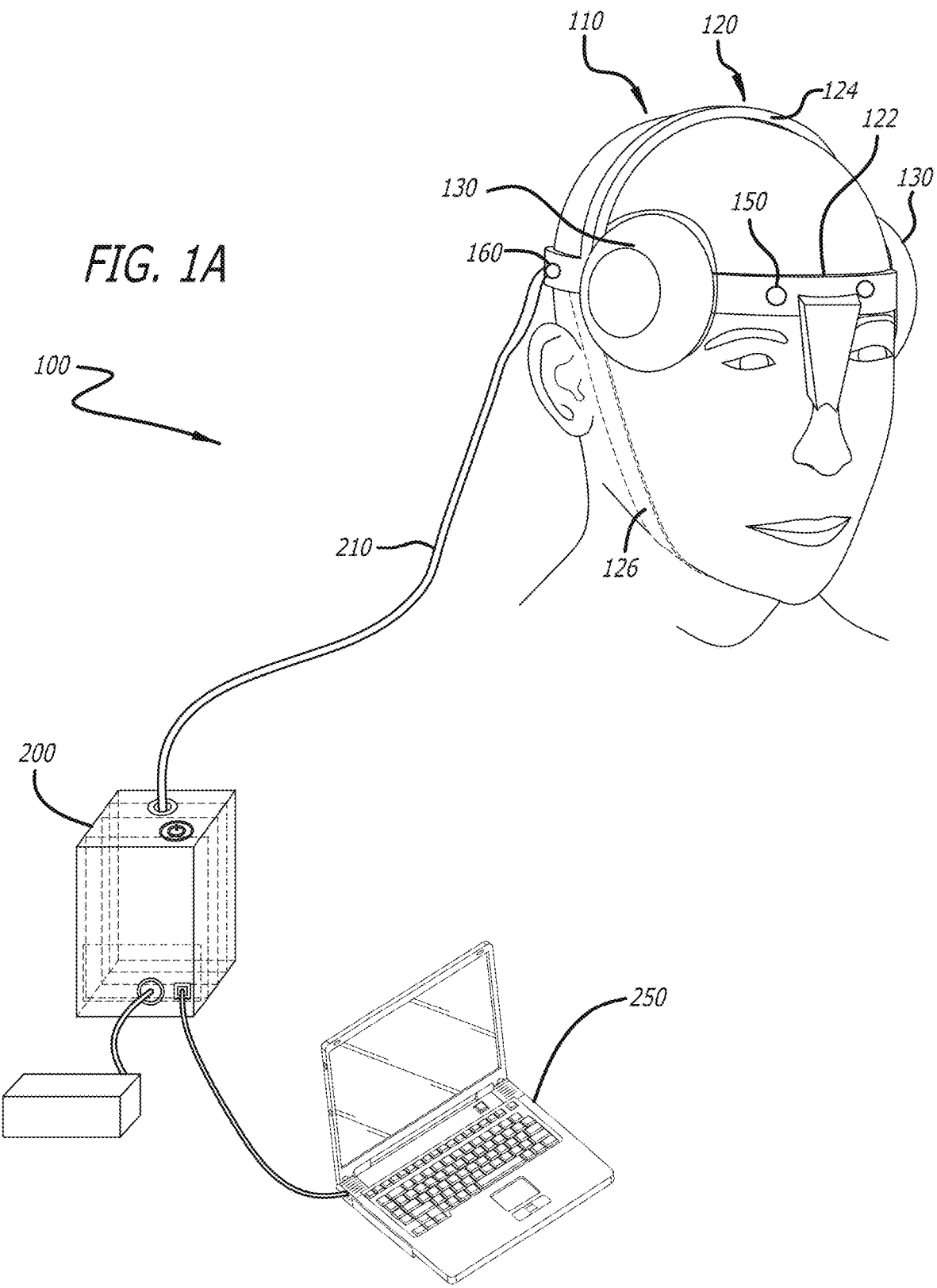
FIGS. 1A-B is a schematic of an exemplary neuromodulation system disclosed herein with FIG. 1A showing a neuromodulation device and a stimulation control computing environment disclosed herein.

The sleep-wake cycle is a neurobiological pattern of activity (wake cycle) alternating with restfulness (sleep cycle). The wake cycle or wakefulness is the period when brain activity is at its highest. EEG brain activity shows, as measured using an electroencephelogram (EEG), frequencies of between 15 Hz to 50 Hz, amplitudes of less than 50 mV and faintly discernable waveform types. In addition, as compared to the sleep cycle, skeletal muscles are tonic and active and heart and respiration rates are regular and at their highest levels.

The sleep cycle is more complex, being divided into five stages, with each having characteristic brainwave frequencies, amplitudes, and waveform type, along with other distinguishable biologic rhythms including eye movements (EOG) and muscle movements (EMG). The first four stages (N1, N2, and N3) of the sleep cycle are categorized as non-Rapid Eye Movement (NREM) sleep while the fifth stage (R) is categorized as Rapid Eye Movement (REM)

sleep. N1 of NREM sleep is the lightest stage of sleep where brainwave activity is slightly slower than during the wake cycle. During this stage, EEG brain activity shows frequencies of between 4 Hz to 12 Hz, relatively low amplitude compared to other stages of consciousness, and a waveform type comprising alpha waves. During N1 eye movement is very slow, skeletal muscle tone is present and breathing occurs at a regular rate.

N2 of non-REM sleep usually follows N1 and represents a deeper sleep. During this stage, EEG brain activity continue to slow with frequencies of between 4 Hz to 8 Hz, relatively low amplitudes compared to other stages of consciousness, and a waveform type comprising theta waves which include specific bursts of rapid activity known as sleep spindles intermixed with sleep structures known as K complexes. During N2 there is no eye movement, skeletal muscle activity decreases and heart and respiration rates are depressed but regular. Stage N2 of NREM sleep comprises approximately 40-60% of total sleep time.

Stage N3 of NREM sleep is a progressively deeper stage of sleep called Slow Wave Sleep (SWS) or deep sleep and is the most restorative stage of sleep. During this stage, EEG brain activity shows increased spectral power at frequencies of between 0.5 Hz to 4 Hz, relatively high amplitudes compared to other stages of consciousness, and a waveform type comprising delta waves or slow waves. During N3 there is no eye movement, skeletal muscle activity decreases and heart and respiration rates are depressed but regular. Stage of N3 NREM sleep comprises approximately 5-15% of total sleep time.

REM is the stage of sleep associated with dreaming. During this stage, EEG brain activity shows increased spectral power at frequencies of between 15 Hz to 30 Hz, relatively low amplitudes compared to other stages of consciousness, and eye movement is rapid. Although brainwave activity and eye movement resemble the wake cycle, skeletal muscles are atonic or without movement and heart and respiration rates are faster and more erratic and irregular than during NREM sleep. Following REM, the sleep cycle resumes starting with periods of N1, N2 and N3 of NREM sleep intermixed before returning to REM sleep again for longer periods of time as sleep time continues.

Although sleep is a highly heterogeneous state, composed of local and global network oscillatory states, its parts disproportionately contribute to its beneficial effects. Slow wave sleep observed in Stage N3 of NREM sleep is largely derived from network synchronization between the thalamus deep within the brain and superficial cortical layers of the brain. The peak of slow waves known as the cortical "Up" state is preceded by a burst of thalamic activity, intrinsically coupling activation of the thalamus to slow wave amplitude. These waves may permeate all states of sleep but are more prominent during Stage N2 and N3 NREM sleep. While the canonical function of SWS is to drive memory consolidation, or the stabilization of long-term memories it is also critical for both cognitive and physiological functions and brain tissue repair. Disrupting slow waves within the sleep period results in detriment to attention and focus in human subjects and creates a general state of fatigue. Interestingly, the countervailing intervention is also supported; by increasing the amplitude of slow waves during NREM sleep, cognitive processes are markedly improved. Collectively, enhancing slow waves is an opportunity to improve both cognitive and physiological functions.

The present specification discloses a neuromodulation system comprising a wearable neuromodulation device integrated with EEG electrodes and one or more integrated ultrasound transducer arrays. The disclosed neuromodulation system further includes a stimulation control unit comprising one or more processors, and software that operates and controls the features and functionality of the ultrasound stimulation when executed by such processors. Such software includes, without limitation, EEG real-time analysis software that can continuously monitor brain functionality to identify one or more certain characteristics, phases or states of brain activity, and brain mapping software that can plot one or more specific region of the brain and accurately focus or steer ultrasound stimulation to that one or more specific brain regions. The disclosed neuromodulation system also includes a computational device that aids in neuromodulation device operation and data storage of collected information. Thus, a neuromodulation system disclosed herein non-invasively administers ultrasound stimulation in a spatially and temporally controlled manner. As such, a device disclosed herein enables a focus application of ultrasound stimulation to a specified region of the brain that largely excludes surrounding brain tissue.

In particular, a neuromodulation device disclosed herein administers focused ultrasound stimulation that drives neural activity by targeting the thalamus and other core structures regulating SWS residing deep in the brain to maximize intervention impact on wave enhancement, such as slow wave enhancement. Because slow waves can be enhanced by exciting cells during the "up state" of slow waves, or by inhibiting cells during the "down state" the device will need to collect and analyze real time EEG signal, automatically stage the sleep, and apply ultrasonic stimulation to the thalamus during slow wave peak phase. By leveraging advances disclosed herein, a neuromodulation device disclosed herein improves beam focusing and temporal neural interaction with thalamic regions on multiple levels.

Unlike devices utilizing electrical or sensory stimulation, ultrasound stimulation can be focused onto deep regions of the brain without impacting overlying tissue through the same principles that allow light to be focused through a lens. By comparison, tDCS employs electrical current across the skull in efforts to generate sufficient current across the cortex, although, this current is comparatively weaker than that which is required to elicit neuronal response at typical operating voltages. Accordingly, it is difficult if not impossible to accurately phase target in series where electrical stimulation interferes with electrical signal readout. As such, electrical stimulation must be intermittent, or inaccurately delivered in series. On the other hand, a device disclosed herein overcome this obstacle and provide focused ultrasound providing pressure fields to stimulate specific neural tissue/areas. Since electrical current is not employed in a neuromodulation device disclosed herein, there is no electrical interference, thereby making serial phase targeted stimulation possible.

Aspects of the present specification disclose a neuromodulation device. A neuromodulation device disclosed herein is a low profile, cranial mounted device. In some embodiments, a neuromodulation device disclosed herein is suitable for wear during sleep without compromising device functionality, delivers spatially targeted and safe ultrasonic pressure fields through skull, and properly classifies sleep stage and slow wave phase for well-timed stimulus delivery.

Figure 1B:
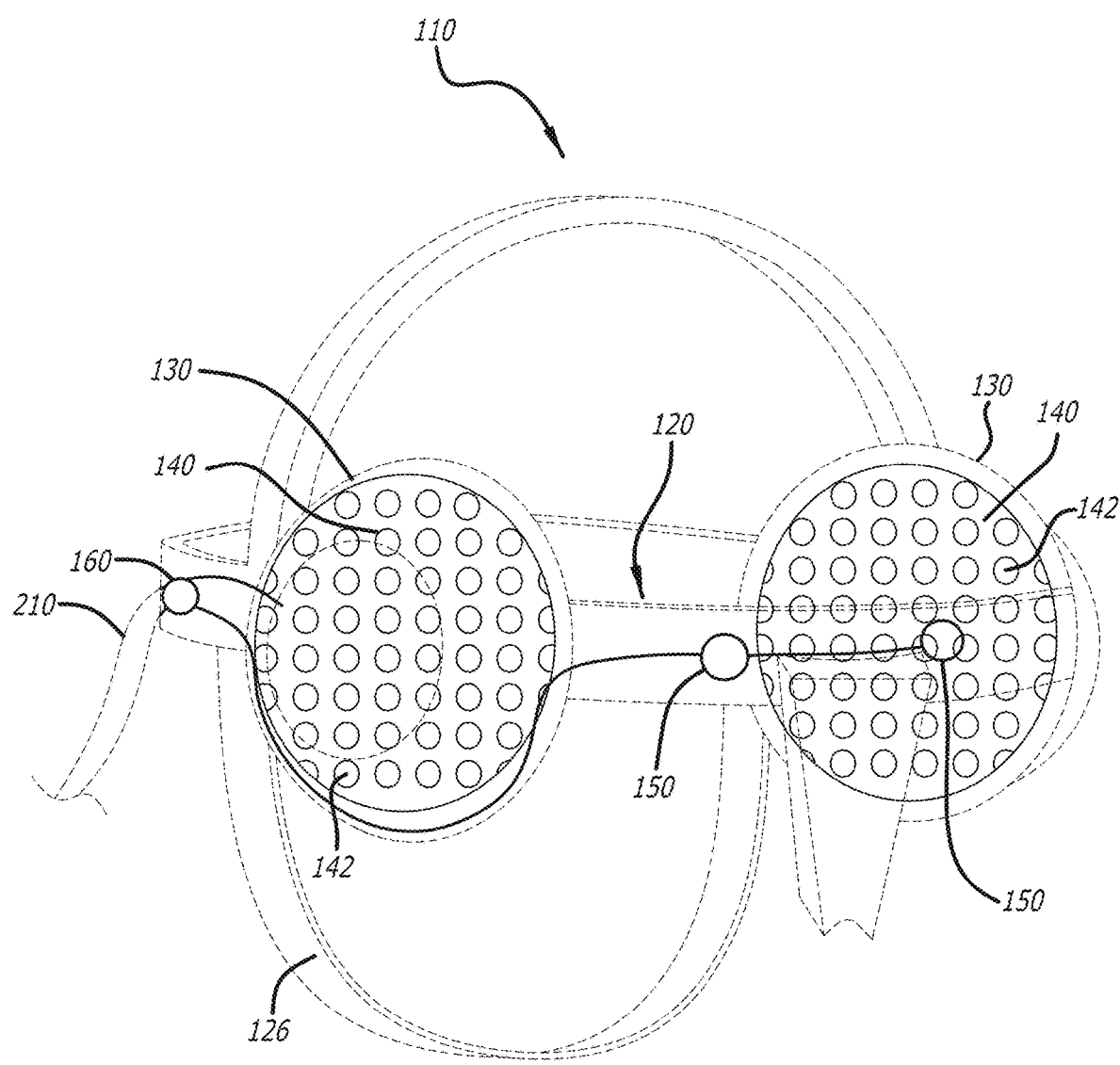

In some embodiments, and as shown in FIGS. 1A-B, an exemplary neurostimulator device 110 comprises a wearable device housing 120, which supports two array housings 130 each containing an ultrasound transducer 140, and two EEG electrodes 150, such as, e.g., active dry EEG electrodes. When worn, wearable device housing 120 is configured to encircle the cranium in a transverse plane that positions the main band along the forehead, temples and back of the head. Wearable device housing 120 provides rigid stereotactic placement of ultrasound transducer arrays 140 over the temporal region of the user's head as well as positions EEG electrodes 150 flat against the user's forehead.

Wearable device housing 120 can include a main band, a secondary band, and an optional securing strap. A main band 122, a secondary band 124, and an optional securing strap 126. Main band 122, secondary band 124 and securing strap 126 can be adjustable to facilitate accurate positioning and securing of neuromodulation device 110 to a user's cranium. Secondary band 124 can be attached to main band 122 via first and second secondary band attachment points and configured to extend over the top of the head. First and second vascular disorders by injection of a neurotoxin through the nostrils. attachment points can be static or configured to allow movement between secondary band 124 and main band 122. Optional securing strap 126 is attached to main band 122 via first and second securing strap attachment points and configured to extend under the chin. First and second securing strap attachment points can be static or configured to allow movement between securing strap 126 and main band 122. In aspects of these embodiments, main band 122 has front and back portions composed of a semi-rigid material and side or temple portions composed of a flexible material, secondary band 124 and a first and second attachment hubs each being composed of a semi-rigid material, and a securing strap being composed of an elastic material.

Aspects of the present specification disclose a neuromodulation device comprising an ultrasound transducer array. An ultrasound transducer array disclosed herein is an array of ultrasound-emitting elements designed to provide optimal beam profile shape, steering range, and power output in order to effectively stimulate a specified brain region in a spatial and temporal manner. An ultrasound signal generated by an ultrasound transducer array disclosed herein can be amplified using software, such as, e.g., frequency specific MOSFET drivers, executed by one or more processors of a stimulation control unit disclosed herein. As such, the arrangement of ultrasound-emitting elements within an ultrasound transducer array, the number of ultrasound-emitting elements used in an ultrasound transducer array, the maximum output pressure the ultrasound-emitting elements used in an ultrasound transducer array, the spacing between each ultrasound-emitting element within an ultrasound transducer array and ultrasound signal amplification each have a bearing on the optimal functionality of a neuromodulation device disclosed herein. For example, increasing the number of ultrasound-emitting elements or reducing each elements diameter increases the steering capacity an ultrasound transducer array. In addition, increasing the spacing between each ultrasound-emitting element enables the generation of a smaller beam width while employing a two-dimensional arrangement enables focal steering. Generally, the more ultrasound-emitting elements employed and the larger dimensional arrangement of those ultrasound-emitting elements, then the smaller minimal focal point that can be achieved by the transducer array.

Neuromodulation device 110 comprises one or more ultrasound transducer arrays contain in a housing attached to main band 122 of wearable device housing 120. The one or more ultrasound transducer arrays are located on the inner surface of main band 122 and configured to interface with a user's cranium. In some embodiments, a neuromodulation device disclosed herein contains a single ultrasound transducer array located on the main band. In some embodiments, neuromodulation device 110 contains a single ultrasound transducer array located on one side of main band 122 positioned at either the left or right temple region of a user above the ears. In some embodiments, neuromodulation device 110 contains a single ultrasound transducer array located on each side of main band 122 positioned at the left and right temple region of a user above the ears. In some embodiments, neuromodulation device 110 contains multiple ultrasound transducer arrays located on each side of main band 122 positioned at the left and right temple region of a user above the ears. In aspects of these embodiments, and as shown in FIG. 1A-B, neuromodulation device 110 comprises two ultrasound transducer arrays 140 one located on the left side of main band 122 and one located on the right side of main band 122. In aspects of these embodiments, neuromodulation device 110 comprises two ultrasound transducer arrays located on the left side of main band 122 and two ultrasound transducer arrays located on the right side of main band 122.

In some embodiments, an ultrasound transducer array disclosed herein is about 50 mm diameter and contains 64 element sparse element arrays made of a diced PZT composite material. The width and composition of the PZT composite are designed to operate at 700 KHz. The elements are wired to their signal input source using a printed flex circuit which is all maintained inside the housing unit. A matching layer is coupled to the inner surface of the transducer and further coupled to a silicone pad pressed against the temporal window of the user with >1 Newton force.

An ultrasound transducer array disclosed herein comprises a planar, open-curved arc, or closed-curved arc configuration of ultrasound-emitting elements. The planar, open-curved arc, or closed-curved arc configuration of ultrasound-emitting elements used in an ultrasound transducer array disclosed herein is a configuration designed to provide optimal beam shape, steering range, and power output in order to effectively stimulate a specified brain region in a spatial and temporal manner. In some embodiments, an ultrasound transducer array disclosed herein is a one-dimensional planar, curved or closed curved arc configuration of ultrasound-emitting elements. In some embodiments, each ultrasound-emitting element can be controlled in isolation, or in clusters to reduce cabling.

A neuromodulation device can comprise a single comprises a ultrasound transducer array or a plurality of ultrasound transducer array. The number of ultrasound transducer arrays disclosed herein is a number designed to provide optimal delivery of ultrasound to a specified brain region in a spatial and temporal manner. In aspects of this embodiment, a neuromodulation device disclosed herein comprises, e.g., 1, 2, 3, 4, 5, 6, 7, 8, 9 or 10 ultrasound transducer arrays. In aspects of this embodiment, a neuromodulation device disclosed herein comprises, e.g., at least 2, at least 3, at least 4, at least 5, at least 6, at least 7, at least 8, at least 9 or at least 10 ultrasound transducer arrays. In yet aspects of this embodiment, a neuromodulation device disclosed herein comprises, e.g., at most 2, at most 3, at most 4, at most 5, at most 6, at most 7, at most 8, at most 9 or at most 10 ultrasound transducer arrays. In still aspects of this embodiment, a neuromodulation device disclosed herein comprises, e.g., at 2-3 ultrasound transducer arrays, 2-4 ultrasound transducer arrays, 2-5 ultrasound transducer arrays, 2-6 ultrasound transducer arrays, 2-7 ultrasound transducer arrays, 2-8 ultrasound transducer arrays, 2-9 ultrasound transducer arrays, 2-10 ultrasound transducer arrays, 3-4 ultrasound transducer arrays, 3-5 ultrasound transducer arrays, 3-6 ultrasound transducer arrays, 3-7 ultrasound transducer arrays, 3-8 ultrasound transducer arrays, 3-9 ultrasound transducer arrays, 3-10 ultrasound transducer arrays, 4-5 ultrasound transducer arrays, 4-6 ultrasound transducer arrays, 4-7 ultrasound transducer arrays, 4-8 ultrasound transducer arrays, 4-9 ultrasound transducer arrays, 4-10 ultrasound transducer arrays, 5-6 ultrasound transducer arrays, 5-7 ultrasound transducer arrays, 5-8 ultrasound transducer arrays, 5-9 ultrasound transducer arrays, 5-10 ultrasound transducer arrays, 6-7 ultrasound transducer arrays, 6-8 ultrasound transducer arrays, 6-9 ultrasound transducer arrays, 6-10 ultrasound transducer arrays, 7-8 ultrasound transducer arrays, 7-9 ultrasound transducer arrays, 7-10 ultrasound transducer arrays, 8-9 ultrasound transducer arrays, 8-10 ultrasound transducer arrays, or 9-10 ultrasound transducer arrays.

In some embodiments, an ultrasound transducer array disclosed herein comprises a two-dimensional planar, open-curved arc, or closed-curved arc configuration of ultrasound-emitting elements. In aspects of these embodiments, a two-dimensional planar, open-curved arc, or closed-curved arc configuration of an ultrasound transducer array can comprise, e.g., 2, 3, 4, 5, 6, 7, or 8 rows of ultrasound-emitting elements. In other aspects of these embodiments, a two-dimensional planar, curved or closed curved arc configuration of an ultrasound transducer array can comprise, e.g., at least 2, at least 3, at least 4, at least 5 rows, at least 6 rows, at least 7 rows, or at least 8 rows of ultrasound-emitting elements. In yet other aspects of these embodiments, a two-dimensional planar, curved or closed curved arc configuration of ultrasound transducer array can comprise, e.g., at most 2, at most 3, at most 4, at most 5 rows, at most 6 rows, at most 7 rows, or at most 8 rows of ultrasound-emitting elements. In still other aspects of these embodiments, a two-dimensional planar, curved or closed curved arc configuration of ultrasound transducer array can comprise, e.g., 2-3 rows of ultrasound-emitting elements, 2-4 rows of ultrasound-emitting elements, 2-5 rows of ultrasound-emitting elements, 2-6 rows of ultrasound-emitting elements, 2-7 rows of ultrasound-emitting elements, 2-8 rows of ultrasound-emitting elements, 3-4 rows of ultrasound-emitting elements, 3-5 rows of ultrasound-emitting elements, 3-6 rows of ultrasound-emitting elements, 3-7 rows of ultrasound-emitting elements, 3-8 rows of ultrasound-emitting elements, 4-5 rows of ultrasound-emitting elements, 4-6 rows of ultrasound-emitting elements, 4-7 rows of ultrasound-emitting elements, 4-8 rows of ultrasound-emitting elements, 5-6 rows of ultrasound-emitting elements, 5-7 rows of ultrasound-emitting elements, 5-8 rows of ultrasound-emitting elements, 6-7 rows of ultrasound-emitting elements, 6-8 rows of ultrasound-emitting elements, or 7-8 rows of ultrasound-emitting elements.

An ultrasound transducer array comprises a plurality of ultrasound-emitting elements. The number of ultrasound-emitting elements comprising an ultrasound transducer array disclosed herein is a number designed to provide optimal beam shape, steering range, and power output in order to effectively stimulate a specified brain region in a spatial and temporal manner. In aspects of this embodiment, an ultrasound transducer array comprises, e.g., 1, 2, 3, 4, 5, 6, 7, 8, 9 or 10 ultrasound-emitting elements. In aspects of this embodiment, an ultrasound transducer array comprises, e.g., at least 2, at least 3, at least 4, at least 5, at least 6, at least 7, at least 8, at least 9 or at least 10 ultrasound-emitting elements. In yet aspects of this embodiment, an ultrasound transducer array comprises, e.g., at most 2, at most 3, at most 4, at most 5, at most 6, at most 7, at most 8, at most 9 or at most 10 ultrasound-emitting elements. In still aspects of this embodiment, an ultrasound transducer array comprises, e.g., at 2-3 ultrasound-emitting elements, 2-4 ultrasound-emitting elements, 2-5 ultrasound-emitting elements, 2-6 ultrasound-emitting elements, 2-7 ultrasound-emitting elements, 2-8 ultrasound-emitting elements, 2-9 ultrasound-emitting elements, 2-10 ultrasound-emitting elements, 3-4 ultrasound-emitting elements, 3-5 ultrasound-emitting elements, 3-6 ultrasound-emitting elements, 3-7 ultrasound-emitting elements, 3-8 ultrasound-emitting elements, 3-9 ultrasound-emitting elements, 3-10 ultrasound-emitting elements, 4-5 ultrasound-emitting elements, 4-6 ultrasound-emitting elements, 4-7 ultrasound-emitting elements, 4-8 ultrasound-emitting elements, 4-9 ultrasound-emitting elements, 4-10 ultrasound-emitting elements, 5-6 ultrasound-emitting elements, 5-7 ultrasound-emitting elements, 5-8 ultrasound-emitting elements, 5-9 ultrasound-emitting elements, 5-10 ultrasound-emitting elements, 6-7 ultrasound-emitting elements, 6-8 ultrasound-emitting elements, 6-9 ultrasound-emitting elements, 6-10 ultrasound-emitting elements, 7-8 ultrasound-emitting elements, 7-9 ultrasound-emitting elements, 7-10 ultrasound-emitting elements, 8-9 ultrasound-emitting elements, 8-10 ultrasound-emitting elements, or 9-10 ultrasound-emitting elements.

In aspects of this embodiment, each row of an ultrasound transducer array comprises, e.g., 4, 8, 12, 16, 20, 24, 28, 32, 36, 40, 44, 48, 52, 56, 60 or 64 ultrasound-emitting elements. In other aspects of this embodiment, each row of an ultrasound transducer array comprises, e.g., at least 4, at least 8, at least 12, at least 16, at least 20, at least 24, at least 28, at least 32, at least 36, at least 40, at least 44, at least 48, at least 52, at least 56, at least 60 or at least 64 ultrasound-emitting elements. In yet other aspects of this embodiment, each row of an ultrasound transducer array comprises, e.g., at most 4, at most 8, at most 12, at most 16, at most 20, at most 24, at most 28, at most 32, at most 36, at most 40, at most 44, at most 48, at most 52, at most 56, at most 60 or at most 64 ultrasound-emitting elements. In yet other aspects of this embodiment, each row of an ultrasound transducer array comprises, e.g., 4-8 ultrasound-emitting elements, 4-12 ultrasound-emitting elements, 4-16 ultrasound-emitting elements, 4-20 ultrasound-emitting elements, 4-24 ultrasound-emitting elements, 4-28 ultrasound-emitting elements, 4-32 ultrasound-emitting elements, 4-36 ultrasound-emitting elements, 4-40 ultrasound-emitting elements, 4-44 ultrasound-emitting elements, 4-48 ultrasound-emitting elements, 4-52 ultrasound-emitting elements, 4-56 ultrasound-emitting elements, 4-60 ultrasound-emitting elements, 4-64 ultrasound-emitting elements, 8-12 ultrasound-emitting elements, 8-16 ultrasound-emitting elements, 8-20 ultrasound-emitting elements, 8-24 ultrasound-emitting elements, 8-28 ultrasound-emitting elements, 8-32 ultrasound-emitting elements, 8-36 ultrasound-emitting elements, 8-40 ultrasound-emitting elements, 8-44 ultrasound-emitting elements, 8-48 ultrasound-emitting elements, 8-52 ultrasound-emitting elements, 8-56 ultrasound-emitting elements, 8-60 ultrasound-emitting elements, 8-64 ultrasound-emitting elements, 12-16 ultrasound-emitting elements, 12-20 ultrasound-emitting elements, 12-24 ultrasound-emitting elements, 12-28 ultrasound-emitting elements, 12-32 ultrasound-emitting elements, 12-36 ultrasound-emitting elements, 12-40 ultrasound-emitting elements, 12-44 ultrasound-emitting elements, 12-48 ultrasound-emitting elements, 12-52 ultrasound-emitting elements, 12-56 ultrasound-emitting elements, 12-60 ultrasound-emitting elements, 12-64 ultrasound-emitting elements, 16-20 ultrasound-emitting elements, 16-24 ultrasound-emitting elements, 16-28 ultrasound-emitting elements, 16-32 ultrasound-emitting elements, 16-36 ultrasound-emitting elements, 16-40 ultrasound-emitting elements, 16-44 ultrasound-emitting elements, 16-48 ultrasound-emitting elements, 16-52 ultrasound-emitting elements, 16-56 ultrasound-emitting elements, 16-60 ultrasound-emitting elements, 16-64 ultrasound-emitting elements, 20-24 ultrasound-emitting elements, 20-28 ultrasound-emitting elements, 20-32 ultrasound-emitting elements, 20-36 ultrasound-emitting elements, 20-40 ultrasound-emitting elements, 20-44 ultrasound-emitting elements, 20-48 ultrasound-emitting elements, 20-52 ultrasound-emitting elements, 20-56 ultrasound-emitting elements, 20-60 ultrasound-emitting elements, 20-64 ultrasound-emitting elements, 24-28 ultrasound-emitting elements, 24-32 ultrasound-emitting elements, 24-36 ultrasound-emitting elements, 24-40 ultrasound-emitting elements, 24-44 ultrasound-emitting elements, 24-48 ultrasound-emitting elements, 24-52 ultrasound-emitting elements, 24-56 ultrasound-emitting elements, 24-60 ultrasound-emitting elements, 24-64 ultrasound-emitting elements, 28-32 ultrasound-emitting elements, 28-36 ultrasound-emitting elements, 28-40 ultrasound-emitting elements, 28-44 ultrasound-emitting elements, 28-48 ultrasound-emitting elements, 28-52 ultrasound-emitting elements, 28-56 ultrasound-emitting elements, 28-60 ultrasound-emitting elements, 28-64 ultrasound-emitting elements, 32-36 ultrasound-emitting elements, 32-40 ultrasound-emitting elements, 32-44 ultrasound-emitting elements, 32-48 ultrasound-emitting elements, 32-52 ultrasound-emitting elements, 32-56 ultrasound-emitting elements, 32-60 ultrasound-emitting elements, 32-64 ultrasound-emitting elements, 36-40 ultrasound-emitting elements, 36-44 ultrasound-emitting elements, 36-48 ultrasound-emitting elements, 36-52 ultrasound-emitting elements, 36-56 ultrasound-emitting elements, 36-60 ultrasound-emitting elements, 36-64 ultrasound-emitting elements, 40-44 ultrasound-emitting elements, 40-48 ultrasound-emitting elements, 40-52 ultrasound-emitting elements, 40-56 ultrasound-emitting elements, 40-60 ultrasound-emitting elements, 40-64 ultrasound-emitting elements, 44-48 ultrasound-emitting elements, 44-52 ultrasound-emitting elements, 44-56 ultrasound-emitting elements, 44-60 ultrasound-emitting elements, 44-64 ultrasound-emitting elements, 48-52 ultrasound-emitting elements, 48-56 ultrasound-emitting elements, 48-60 ultrasound-emitting elements, 48-64 ultrasound-emitting elements, 52-56 ultrasound-emitting elements, 52-60 ultrasound-emitting elements, 52-64 ultrasound-emitting elements, 56-60 ultrasound-emitting elements, 56-64 ultrasound-emitting elements, or 60-64 ultrasound-emitting elements.

In aspects of this embodiment, an ultrasound transducer array comprises, e.g., 4, 8, 12, 16, 24, 32, 48, 64, 80, 96, 108, 128, 144, or 256 ultrasound-emitting elements. In other aspects of this embodiment, an ultrasound transducer array comprises, e.g., at least 4, at least 8, at least 12, at least 16, at least 24, at least 32, at least 48, at least 64, at least 80, at least 96, at least 108, at least 128, at least 144, or at least 254 ultrasound-emitting elements. In yet other aspects of this embodiment, an ultrasound transducer array comprises, e.g., at most 4, at most 8, at most 12, at most 16, at most 24, at most 32, at most 48, at most 64, at most 80, at most 96, at most 108, at most 128, at most 144, or at most 254 ultrasound-emitting elements. In still other aspects of this embodiment, an ultrasound transducer array comprises, e.g., 4-8 ultrasound-emitting elements, 4-12 ultrasound-emitting elements, 4-16 ultrasound-emitting elements, 4-24 ultrasound-emitting elements, 4-32 ultrasound-emitting elements, 4-36 ultrasound-emitting elements, 4-48 ultrasound-emitting elements, 8-12 ultrasound-emitting elements, 8-16 ultrasound-emitting elements, 8-24 ultrasound-emitting elements, 8-32 ultrasound-emitting elements, 8-36 ultrasound-emitting elements, 8-48 ultrasound-emitting elements, 8-60 ultrasound-emitting elements, 16-24 ultrasound-emitting elements, 16-32 ultrasound-emitting elements, 16-36 ultrasound-emitting elements, 16-48 ultrasound-emitting elements, 16-60 ultrasound-emitting elements, 16-72 ultrasound-emitting elements, 24-32 ultrasound-emitting elements, 24-36 ultrasound-emitting elements, 24-48 ultrasound-emitting elements, 24-60 ultrasound-emitting elements, 24-72 ultrasound-emitting elements, 24-80 ultrasound-emitting elements, 24-96 ultrasound-emitting elements, 36-48 ultrasound-emitting elements, 36-60 ultrasound-emitting elements, 36-72 ultrasound-emitting elements, 36-80 ultrasound-emitting elements, 36-96 ultrasound-emitting elements, 36-108 ultrasound-emitting elements, 36-128 ultrasound-emitting elements, 48-60 ultrasound-emitting elements, 48-72 ultrasound-emitting elements, 48-80 ultrasound-emitting elements, 48-96 ultrasound-emitting elements, 48-108 ultrasound-emitting elements, 48-128 ultrasound-emitting elements, 72-96 ultrasound-emitting elements, 72-108 ultrasound-emitting elements, 72-128 ultrasound-emitting elements, 72-144 ultrasound-emitting elements, or 72-256 ultrasound-emitting elements.

An ultrasound transducer array disclosed herein provides properly timed output pressure from the ultrasound-emitting elements designed to provide optimal beam shape, spatial focus, and power output in order to effectively stimulate a specified brain region in a spatial and temporal manner. In aspects of this embodiment, an ultrasound transducer array disclosed herein provides an operating frequency from the ultrasound-emitting elements of, e.g., about 200 kHz, about 250 kHz, about 300 kHz, about 350 kHz, about 400 kHz, about 450 kHz, about 500 kHz, about 600 kHz, about 650 kHz, about 700 kHz, about 750 kHz, about 800 kHz, about 850 kHz, about 900 kHz, about 950 kHz, or about 1 MHz. In other aspects of this embodiment, an ultrasound transducer array disclosed herein provides an operating frequency of the ultrasound-emitting elements of, e.g., at least 50 kHz, at least 100 kHz, at least 150 kHz, at least 200 kHz, at least 250 kHz, at least 300 kHz, at least 350 kHz, at least 400 kHz, at least 450 kHz, at least 500 KHz or at least 1 MHz. In yet other aspects of this embodiment, an ultrasound transducer array disclosed herein provides an operating frequency of the ultrasound-emitting elements of, e.g., at most 50 kHz, at most 100 kHz, at most 150 kHz, at most 200 kHz, at most 250 kHz, at most 300 kHz, at most 350 kHz, at most 400 kHz, at most 450 kHz, at most 500 kHz, or at most 1 MHz. In still other aspects of this embodiment, an ultrasound transducer array disclosed herein provides an operating frequency of the ultrasound-emitting elements of, e.g., about 50 kHz to about 100 kHz, about 50 kHz to about 200 kHz, about 50 kHz to about 300 kHz, about 50 kHz to about 400 kHz, about 50 kHz to about 500 kHz, about 100 kHz to about 200 kHz, about 100 kHz to about 300 kHz, about 100 kHz to about 400 kHz, about 100 kHz to about 500 kHz, about 150 kHz to about 200 kHz, about 150 kHz to about 300 kHz, about 150 kHz to about 400 kHz, about 150 kHz to about 500 kHz, about 200 kHz to about 300 kHz, about 200 kHz to about 400 kHz, about 200 kHz to about 500 kHz, about 250 kHz to about 300 kHz, about 250 kHz to about 400 kHz, about 250 kHz to about 500 kHz, about 300 kHz to about 400 kHz, about 300 kHz to about 500 kHz, about 350 kHz to about 400 kHz, about 400 kHz to about 500 kHz, about 450 kHz to about 500 kHz.

In aspects of this embodiment, an ultrasound transducer array disclosed herein provides an operating frequency from the ultrasound-emitting elements of, e.g., about 500 kHz, about 600 kHz, about 700 kHz, about 800 kHz, about 900 kHz, about 1000 kHz, about 1,100 kHz, about 1,200 kHz, about 1,300 kHz, about 1,400 kHz, or about 1,500 kHz. In other aspects of this embodiment, an ultrasound transducer array disclosed herein provides an output power from the ultrasound-emitting elements of, e.g., at least 500 kHz, at least 600 kHz, at least 700 kHz, at least 800 kHz, at least 900 kHz, at least 1000 kHz, at least 1,100 kHz, at least 1,200 kHz, at least 1,300 kHz, at least 1,400 kHz, or at least 1,500 kHz. In yet other aspects of this embodiment, an ultrasound transducer array disclosed herein provides an operating frequency from the ultrasound-emitting elements of, e.g., at most 500 kHz, at most 600 kHz, at most 700 kHz, at most 800 kHz, at most 900 kHz, at most 1000 kHz, at most 1,100 kHz, at most 1,200 kHz, at most 1,300 kHz, at most 1,400 kHz, or at most 1,500 kHz. In still other aspects of this embodiment, an ultrasound transducer array disclosed herein provides an operating frequency from the ultrasound-emitting elements of, e.g., about 500 kHz to about 600 kHz, about 500 kHz to about 700 kHz, about 500 kHz to about 800 kHz, about 500 kHz to about 900 kHz, about 500 kHz to about 1,000 kHz, about 500 kHz to about 1,100 kHz, about 500 kHz to about 1,200 kHz, about 500 kHz to about 1,300 kHz, about 500 kHz to about 1,400 kHz, about 500 kHz to about 1,500 kHz, about 600 kHz to about 700 kHz, about 600 kHz to about 800 kHz, about 600 kHz to about 900 kHz, about 600 kHz to about 1,000 kHz, about 600 kHz to about 1,100 kHz, about 600 kHz to about 1,200 kHz, about 600 kHz to about 1,300 kHz, about 600 kHz to about 1,400 kHz, about 600 kHz to about 1,500 kHz, about 700 kHz to about 800 kHz, about 700 kHz to about 900 kHz, about 700 kHz to about 1,000 kHz, about 700 kHz to about 1,100 kHz, about 700 kHz to about 1,200 kHz, about 700 kHz to about 1,300 kHz, about 700 kHz to about 1,400 kHz, about 700 kHz to about 1,500 kHz, about 800 kHz to about 900 kHz, about 800 kHz to about 1,000 kHz, about 800 kHz to about 1,100 kHz, about 800 kHz to about 1,200 kHz, about 800 kHz to about 1,300 kHz, about 800 kHz to about 1,400 kHz, about 800 kHz to about 1,500 kHz, about 900 kHz to about 1,000 kHz, about 900 kHz to about 1,100 kHz, about 900 kHz to about 1,200 kHz, about 900 kHz to about 1,300 kHz, about 900 kHz to about 1,400 kHz, about 900 kHz to about 1,500 kHz, about 1,000 kHz to about 1,100 kHz, about 1,000 kHz to about 1,200 kHz, about 1,000 kHz to about 1,300 kHz, about 1,000 kHz to about 1,400 kHz, about 1,000 kHz to about 1,500 kHz, about 1,100 kHz to about 1,200 kHz, about 1,100 kHz to about 1,300 kHz, about 1,100 kHz to about 1,400 kHz, about 1,100 kHz to about 1,500 kHz, about 1,200 kHz to about 1,300 kHz, about 1,200 kHz to about 1,400 kHz, about 1,200 kHz to about 1,500 kHz, about 1,300 kHz to about 1,400 kHz, about 1,300 kHz to about 1,500 kHz, or about 1,400 kHz to about 1,500 kHz.

An ultrasound transducer array disclosed herein provides properly timed output pressure from the ultrasound-emitting elements designed to provide optimal beam shape, spatial focus, and power output in order to effectively stimulate a specified brain region in a spatial and temporal manner. In aspects of this embodiment, an ultrasound transducer array disclosed herein provides an output pressure from the ultrasound-emitting elements enabling ultrasound stimulation at a tissue depth of, e.g., 20 mm, 25 mm, 30 mm, 35 mm, 40 mm, 45 mm, 50 mm, 55 mm, 60 mm, 65 mm, 70 mm, 75 mm, 80 mm, 85 mm, 90 mm or 100 mm. In aspects of this embodiment, an ultrasound transducer array disclosed herein provides a focal output pressure from the ultrasound-emitting elements enabling ultrasound stimulation at a tissue depth of, e.g., at least 20 mm, at least 25 mm, at least 30 mm, at least 35 mm, at least 40 mm, at least 45 mm, at least 50 mm, at least 55 mm, at least 60 mm, at least 65 mm, at least 70 mm, at least 75 mm, at least 80 mm, at least 85 mm, at least 90 mm, at least 95 mm, or at least 100 mm. In aspects of this embodiment, an ultrasound transducer array disclosed herein provides an output pressure from the ultrasound-emitting elements enabling ultrasound stimulation at a tissue depth of, e.g., at most 20 mm, at most 25 mm, at most 30 mm, at most 35 mm, at most 40 mm, at most 45 mm, at most 50 mm, at most 55 mm, at most 60 mm, at most 65 mm, at most 70 mm, at most 75 mm, at most 80 mm, at most 85 mm, at most 90 mm, at most 95 mm, or at most 100 mm. In aspects of this embodiment, an ultrasound transducer array disclosed herein provides a focal output pressure from the ultrasound-emitting elements enabling ultrasound stimulation at a tissue depth of, e.g., 20 mm to 25 mm, 20 mm to 30 mm, 20 mm to 35 mm, 20 mm to 40 mm, 20 mm to 45 mm, 20 mm to 50 mm, 20 mm to 55 mm, 20 mm to 60 mm, 20 mm to 70 mm, 20 mm to 80 mm, 20 mm to 90 mm, 20 mm to 100 mm, 25 mm to 30 mm, 25 mm to 35 mm, 25 mm to 40 mm, 25 mm to 45 mm, 25 mm to 50 mm, 25 mm to 55 mm, 25 mm to 60 mm, 25 mm to 70 mm, 25 mm to 80 mm, 25 mm to 90 mm, 25 mm to 100 mm, 30 mm to 35 mm, 30 mm to 40 mm, 30 mm to 45 mm, 30 mm to 50 mm, 30 mm to 55 mm, 30 mm to 60 mm, 30 mm to 70 mm, 30 mm to 80 mm, 30 mm to 90 mm, 30 mm to 100 mm, 35 mm to 40 mm, 35 mm to 45 mm, 35 mm to 50 mm, 35 mm to 55 mm, 35 mm to 60 mm, 35 mm to 70 mm, 35 mm to 80 mm, 35 mm to 90 mm, 35 mm to 100 mm, 40 mm to 45 mm, 40 mm to 50 mm, 40 mm to 55 mm, 40 mm to 60 mm, 40 mm to 70 mm, 40 mm to 80 mm, 40 mm to 90 mm, 40 mm to 100 mm, 45 mm to 50 mm, 45 mm to 55 mm, 45 mm to 60 mm, 45 mm to 70 mm, 45 mm to 80 mm, 45 mm to 90 mm, 45 mm to 100 mm, 50 mm to 55 mm, 50 mm to 60 mm, 50 mm to 70 mm, 50 mm to 80 mm, 50 mm to 90 mm, 50 mm to 100 mm, 55 mm to 60 mm, 55 mm to 70 mm, 55 mm to 80 mm, 55 mm to 90 mm, 55 mm to 100 mm, 60 mm to 70 mm, 60 mm to 80 mm, 60 mm to 90 mm, 60 mm to 100 mm, 70 mm to 80 mm, 70 mm to 90 mm, 70 mm to 100 mm, 80 mm to 90 mm, or 90 mm to 100 mm.

An ultrasound transducer array disclosed herein provides properly timed intensity from the ultrasound-emitting elements designed to provide optimal beam shape, steering range, and power output in order to effectively stimulate a specified brain region in a spatial and temporal manner. In aspects of this embodiment, an ultrasound transducer array disclosed herein provides an spatial peak pulse average intensity at the spatial focus from the ultrasound-emitting elements of, e.g., about 1 $mW/cm^2$, about 2.5 $mW/cm^2$, about 5 $mW/cm^2$, about 7.5 $mW/cm^2$, about 10 $mW/cm^2$, about 15 $mW/cm^2$, about 20 $mW/cm^2$, about 30 $mW/cm^2$, about 40 $mW/cm^2$, about 50 $mW/cm^2$, about 60 $mW/cm^2$, about 70 $mW/cm^2$, about 80 $mW/cm^2$, about 90 $mW/cm^2$, about 100 $mW/cm^2$, about 110 $mW/cm^2$, about 120 $mW/cm^2$, about 130 $mW/cm^2$, about 140 $mW/cm^2$, about 150 $mW/cm^2$, about 160 $mW/cm^2$, about 170 $mW/cm^2$, about 180 $mW/cm^2$, about 190 $mW/cm^2$, or about 200 $mW/cm^2$. In other aspects of this embodiment, an ultrasound transducer array disclosed herein provides an intensity from the ultrasound-emitting elements of, e.g., at least 1 $mW/cm^2$, at least 2.5 $mW/cm^2$, at least 5 $mW/cm^2$, at least 7.5 $mW/cm^2$, at least 10 $mW/cm^2$, at least 15 $mW/cm^2$, at least 20 mW/cm², at least 30 mW/cm², at least 40 mW/cm², at least 50 mW/cm², at least 60 mW/cm², at least 70 mW/cm², at least 80 mW/cm², at least 90 mW/cm², at least 100 mW/cm², at least 110 mW/cm², at least 120 mW/cm², at least 130 mW/cm², at least 140 mW/cm², at least 150 mW/cm², at least 160 mW/cm², at least 170 mW/cm², at least 180 mW/cm², at least 190 mW/cm², or at least 200 mW/cm². In yet other aspects of this embodiment, an ultrasound transducer array disclosed herein provides an intensity from the ultrasound-emitting elements of, e.g., at most 1 mW/cm², at most 2.5 mW/cm², at most 5 mW/cm², at most 7.5 mW/cm², at most 10 mW/cm², at most 15 mW/cm², at most 20 mW/cm², at most 30 mW/cm², at most 40 mW/cm², at most 50 mW/cm², at most 60 mW/cm², at most 70 mW/cm², at most 80 mW/cm², at most 90 mW/cm², at most 100 mW/cm², at most 110 mW/cm², at most 120 mW/cm², at most 130 mW/cm², at most 140 mW/cm², at most 150 mW/cm², at most 160 mW/cm², at most 170 mW/cm², at most 180 mW/cm², at most 190 mW/cm², or at most 200 mW/cm².

In still other aspects of this embodiment, an ultrasound transducer array disclosed herein provides an intensity from the ultrasound-emitting elements of, e.g., about 1 mW/cm² to about 5 mW/cm², about 1 mW/cm² to about 10 mW/cm², about 1 mW/cm² to about 20 mW/cm², about 1 mW/cm² to about 30 mW/cm², about 1 mW/cm² to about 40 mW/cm², about 1 mW/cm² to about 50 mW/cm², about 1 mW/cm² to about 60 mW/cm², about 1 mW/cm² to about 70 mW/cm², about 1 mW/cm² to about 80 mW/cm², about 1 mW/cm² to about 90 mW/cm², about 1 mW/cm² to about 100 mW/cm², about 1 mW/cm² to about 110 mW/cm², about 1 mW/cm² to about 120 mW/cm², about 1 mW/cm² to about 130 mW/cm², about 1 mW/cm² to about 140 mW/cm², about 1 mW/cm² to about 150 mW/cm², about 1 mW/cm² to about 160 mW/cm², about 1 mW/cm² to about 170 mW/cm², about 1 mW/cm² to about 180 mW/cm², about 1 mW/cm² to about 190 mW/cm², about 5 mW/cm² to about 10 mW/cm², about 5 mW/cm² to about 20 mW/cm², about 5 mW/cm² to about 30 mW/cm², about 5 mW/cm² to about 40 mW/cm², about 5 mW/cm² to about 50 mW/cm², about 5 mW/cm² to about 60 mW/cm², about 5 mW/cm² to about 70 mW/cm², about 5 mW/cm² to about 80 mW/cm², about 5 mW/cm² to about 90 mW/cm², about 5 mW/cm² to about 100 mW/cm², about 5 mW/cm² to about 110 mW/cm², about 5 mW/cm² to about 120 mW/cm², about 5 mW/cm² to about 130 mW/cm², about 5 mW/cm² to about 140 mW/cm², about 5 mW/cm² to about 150 mW/cm², about 5 mW/cm² to about 160 mW/cm², about 5 mW/cm² to about 170 mW/cm², about 5 mW/cm² to about 180 mW/cm², about 5 mW/cm² to about 190 mW/cm², about 10 mW/cm² to about 20 mW/cm², about 10 mW/cm² to about 30 mW/cm², about 10 mW/cm² to about 40 mW/cm², about 10 mW/cm² to about 50 mW/cm², about 10 mW/cm² to about 60 mW/cm², about 10 mW/cm² to about 70 mW/cm², about 10 mW/cm² to about 80 mW/cm², about 10 mW/cm² to about 90 mW/cm², about 10 mW/cm² to about 100 mW/cm², about 10 mW/cm² to about 110 mW/cm², about 10 mW/cm² to about 120 mW/cm², about 10 mW/cm² to about 130 mW/cm², about 10 mW/cm² to about 140 mW/cm², about 10 mW/cm² to about 150 mW/cm², about 10 mW/cm² to about 160 mW/cm², about 10 mW/cm² to about 170 mW/cm², about 10 mW/cm² to about 180 mW/cm², about 10 mW/cm² to about 190 mW/cm², about 20 mW/cm² to about 30 mW/cm², about 20 mW/cm² to about 40 mW/cm², about 20 mW/cm² to about 50 mW/cm², about 20 mW/cm² to about 60 mW/cm², about 20 mW/cm² to about 70 mW/cm², about 20 mW/cm² to about 80 mW/cm², about 20 mW/cm² to about 90 mW/cm², about 20 mW/cm² to about 100 mW/cm², about 20 mW/cm² to about 110 mW/cm², about 20 mW/cm² to about 120 mW/cm², about 20 mW/cm² to about 130 mW/cm², about 20 mW/cm² to about 140 mW/cm², about 20 mW/cm² to about 150 mW/cm², about 20 mW/cm² to about 160 mW/cm², about 20 mW/cm² to about 170 mW/cm², about 20 mW/cm² to about 180 mW/cm², about 20 mW/cm² to about 190 mW/cm², about 30 mW/cm² to about 40 mW/cm², about 30 mW/cm² to about 50 mW/cm², about 30 mW/cm² to about 60 mW/cm², about 30 mW/cm² to about 70 mW/cm², about 30 mW/cm² to about 80 mW/cm², about 30 mW/cm² to about 90 mW/cm², about 30 mW/cm² to about 100 mW/cm², about 30 mW/cm² to about 110 mW/cm², about 30 mW/cm² to about 120 mW/cm², about 30 mW/cm² to about 130 mW/cm², about 30 mW/cm² to about 140 mW/cm², about 30 mW/cm² to about 150 mW/cm², about 30 mW/cm² to about 160 mW/cm², about 30 mW/cm² to about 170 mW/cm², about 30 mW/cm² to about 180 mW/cm², about 30 mW/cm² to about 190 mW/cm², about 40 mW/cm² to about 50 mW/cm², about 40 mW/cm² to about 60 mW/cm², about 40 mW/cm² to about 70 mW/cm², about 40 mW/cm² to about 80 mW/cm², about 40 mW/cm² to about 90 mW/cm², about 40 mW/cm² to about 100 mW/cm², about 40 mW/cm² to about 110 mW/cm², about 40 mW/cm² to about 120 mW/cm², about 40 mW/cm² to about 130 mW/cm², about 40 mW/cm² to about 140 mW/cm², about 40 mW/cm² to about 150 mW/cm², about 40 mW/cm² to about 160 mW/cm², about 40 mW/cm² to about 170 mW/cm², about 40 mW/cm² to about 180 mW/cm², about 40 mW/cm² to about 190 mW/cm², about 50 mW/cm² to about 60 mW/cm², about 50 mW/cm² to about 70 mW/cm², about 50 mW/cm² to about 80 mW/cm², about 50 mW/cm² to about 90 mW/cm², about 50 mW/cm² to about 100 mW/cm², about 50 mW/cm² to about 110 mW/cm², about 50 mW/cm² to about 120 mW/cm², about 50 mW/cm² to about 130 mW/cm², about 50 mW/cm² to about 140 mW/cm², about 50 mW/cm² to about 150 mW/cm², about 50 mW/cm² to about 160 mW/cm², about 50 mW/cm² to about 170 mW/cm², about 50 mW/cm² to about 180 mW/cm², about 50 mW/cm² to about 190 mW/cm², about 60 mW/cm² to about 70 mW/cm², about 60 mW/cm² to about 80 mW/cm², about 60 mW/cm² to about 90 mW/cm², about 60 mW/cm² to about 100 mW/cm², about 60 mW/cm² to about 110 mW/cm², about 60 mW/cm² to about 120 mW/cm², about 60 mW/cm² to about 130 mW/cm², about 60 mW/cm² to about 140 mW/cm², about 60 mW/cm² to about 150 mW/cm², about 60 mW/cm² to about 160 mW/cm², about 60 mW/cm² to about 170 mW/cm², about 60 mW/cm² to about 180 mW/cm², about 60 mW/cm² to about 190 mW/cm², about 70 mW/cm² to about 80 mW/cm², about 70 mW/cm² to about 90 mW/cm², about 70 mW/cm² to about 100 mW/cm², about 70 mW/cm² to about 110 mW/cm², about 70 mW/cm² to about 120 mW/cm², about 70 mW/cm² to about 130 mW/cm², about 70 mW/cm² to about 140 mW/cm², about 70 mW/cm² to about 150 mW/cm², about 70 mW/cm² to about 160 mW/cm², about 70 mW/cm² to about 170 mW/cm², about 70 mW/cm² to about 180 mW/cm², about 70 mW/cm² to about 190 mW/cm², about 80 mW/cm² to about 90 mW/cm², about 80 mW/cm² to about 100 mW/cm², about 80 mW/cm² to about 110 mW/cm², about 80 mW/cm² to about 120 mW/cm², about 80 mW/cm² to about 130 mW/cm², about 80 mW/cm² to about 140 mW/cm², about 80 mW/cm² to about 150 mW/cm², about 80 mW/cm² to about 160 mW/cm², about 80 mW/cm² to about 170 mW/cm², about 80 mW/cm² to about 180 mW/cm², about 80 mW/cm² to about 190 mW/cm², about 90 mW/cm² to about 100 mW/cm², about 90 mW/cm² to about 110 mW/cm², about 90 mW/cm² to about 120 mW/cm², about 90 mW/cm² to about 130 mW/cm², about 90 mW/cm² to about 140 mW/cm², about 90 mW/cm² to about 150 mW/cm², about 90 mW/cm² to about 160 mW/cm², about 90 mW/cm² to about 170 mW/cm², about 90 mW/cm² to about 180 mW/cm², about 90 mW/cm² to about 190 mW/cm², about 100 mW/cm² to about 110 mW/cm², about 100 mW/cm² to about 120 mW/cm², about 100 mW/cm² to about 130 mW/cm², about 100 mW/cm² to about 140 mW/cm², about 100 mW/cm² to about 150 mW/cm², about 100 mW/cm² to about 160 mW/cm², about 100 mW/cm² to about 170 mW/cm², about 100 mW/cm² to about 180 mW/cm², about 100 mW/cm² to about 190 mW/cm², about 110 mW/cm² to about 120 mW/cm², about 110 mW/cm² to about 130 mW/cm², about 110 mW/cm² to about 140 mW/cm², about 110 mW/cm² to about 150 mW/cm², about 110 mW/cm² to about 160 mW/cm², about 110 mW/cm² to about 170 mW/cm², about 110 mW/cm² to about 180 mW/cm², about 110 mW/cm² to about 190 mW/cm², about 120 mW/cm² to about 130 mW/cm², about 120 mW/cm² to about 140 mW/cm², about 120 mW/cm² to about 150 mW/cm², about 120 mW/cm² to about 160 mW/cm², about 120 mW/cm² to about 170 mW/cm², about 120 mW/cm² to about 180 mW/cm², about 120 mW/cm² to about 190 mW/cm², about 130 mW/cm² to about 140 mW/cm², about 130 mW/cm² to about 150 mW/cm², about 130 mW/cm² to about 160 mW/cm², about 130 mW/cm² to about 170 mW/cm², about 130 mW/cm² to about 180 mW/cm², about 130 mW/cm² to about 190 mW/cm², about 140 mW/cm² to about 150 mW/cm², about 140 mW/cm² to about 160 mW/cm², about 140 mW/cm² to about 170 mW/cm², about 140 mW/cm² to about 180 mW/cm², about 140 mW/cm² to about 190 mW/cm², about 150 mW/cm² to about 160 mW/cm², about 150 mW/cm² to about 170 mW/cm², about 150 mW/cm² to about 180 mW/cm², about 150 mW/cm² to about 190 mW/cm², about 160 mW/cm² to about 170 mW/cm², about 160 mW/cm² to about 180 mW/cm², about 160 mW/cm² to about 190 mW/cm², about 170 mW/cm² to about 180 mW/cm², about 170 mW/cm² to about 190 mW/cm², or about 180 mW/cm² to about 190 mW/cm².

An ultrasound transducer array disclosed herein provides properly timed ultrasound stimulation pulse from the ultrasound-emitting elements designed to provide optimal beam shape, steering range, and power output in order to effectively stimulate a specified brain region in a spatial and temporal manner. In aspects of this embodiment, an ultrasound transducer array disclosed herein provides an ultrasound stimulation pulse from the ultrasound-emitting elements of, e.g., about 50 msec, about 100 msec, about 150 msec, about 200 msec, about 250 msec, about 300 msec, about 350 msec, about 400 msec, about 450 msec, or about 500 msec. In other aspects of this embodiment, an ultrasound transducer array disclosed herein provides an ultrasound stimulation pulse from the ultrasound-emitting elements of, e.g., at least 50 msec, at least 100 msec, at least 150 msec, at least 200 msec, at least 250 msec, at least 300 msec, at least 350 msec, at least 400 msec, at least 450 msec, or at least 500 msec. In yet other aspects of this embodiment, an ultrasound transducer array disclosed herein provides an ultrasound stimulation pulse from the ultrasound-emitting elements of, e.g., at most 50 msec, at most 100 msec, at most 150 msec, at most 200 msec, at most 250 msec, at most 300 msec, at most 350 msec, at most 400 msec, at most 450 msec, or at most 500 msec. In still other aspects of this embodiment, an ultrasound transducer array disclosed herein provides an ultrasound stimulation pulse from the ultrasound-emitting elements of, e.g., about 50 msec to about 100 msec, about 50 msec to about 150 msec, about 50 msec to about 200 msec, about 50 msec to about 250 msec, about 50 msec to about 300 msec, about 50 msec to about 350 msec, about 50 msec to about 400 msec, about 50 msec to about 450 msec, about 50 msec to about 500 msec, about 100 msec to about 150 msec, about 100 msec to about 200 msec, about 100 msec to about 250 msec, about 100 msec to about 300 msec, about 100 msec to about 350 msec, about 100 msec to about 400 msec, about 100 msec to about 450 msec, about 100 msec to about 500 msec, about 150 msec to about 200 msec, about 150 msec to about 250 msec, about 150 msec to about 300 msec, about 150 msec to about 350 msec, about 150 msec to about 400 msec, about 150 msec to about 450 msec, about 150 msec to about 500 msec, about 200 msec to about 250 msec, about 200 msec to about 300 msec, about 200 msec to about 350 msec, about 200 msec to about 400 msec, about 200 msec to about 450 msec, or about 200 msec to about 500 msec.

An ultrasound transducer array disclosed herein is configured to provide spacing between each ultrasound-emitting element within the ultrasound transducer array in a manner designed to provide optimal beam shape, spatial focus, and power output in order to effectively stimulate a specified brain region in a spatial and temporal manner. In aspects of this embodiment, an ultrasound transducer array is 20 mm, 25 mm, 30 mm, 35 mm, 40 mm, 45 mm, 50 mm, 55 mm, 60 mm, 65 mm, 70 mm, 75 mm, or 80 mm in length and the ultrasound-emitting elements contained therein are equally spaced with one another.

Aspects of the present specification disclose a neuromodulation device comprising an EEG electrode. A neuromodulation device disclosed herein comprises a plurality of EEG electrodes designed to provide optimal measurement of brainwave activity, including, without limitation, wave frequency, wave amplitude, and waveform in order to effectively identify one or more characteristics, phases or states of brain activity. EEG electrodes can be dry electrodes or wet electrodes. A neuromodulation device disclosed herein can further include one or more programmable gain amplifiers that amplify signals obtained from the plurality of EEG electrodes. As such, the arrangement of EEG electrodes, the number of EEG electrodes, the sensitivity the EEG electrodes, the spacing between each EEG electrode, the site of signal amplification, and the capacity of one or more gain amplifiers each have a bearing on the optimal functionality of a neuromodulation device disclosed herein. In some embodiments, an EEG electrode disclosed herein is a replaceable snap on conductive materials with preamplifiers built into the headband. The EEG cabling also resides inside the housing unit. Both the ultrasound and EEG cabling exit the wearable through a port near the back of the head and enters a port into a control unit.

As shown in FIGS. 1A-B, neuromodulation device 110 contains EEG electrodes located on the inner surface of main band 122 and configured to interface with a user's cranium. In some embodiments, neuromodulation device 110 contains a single EEG electrode located on the front portion of main band 122 positioned at the forehead of a user above the eyebrows. In some embodiments, neuromodulation device 110 contains multiple EEG electrodes, each located on the front portion of main band 122 positioned at the forehead of a user above the eyebrows. In aspects of these embodiments, and as shown in FIGS. 1A-B, neuromodulation device disclosed herein comprises two EEG electrodes 150 each located on the front portion of main band 122 with one positioned above the left eyebrow of a user and the other positioned above the right eyebrow of the user.

A single EEG electrode, or a plurality of EEG electrodes comprising a neuromodulation device disclosed herein provides sufficient sensitivity to provide optimal measurement of brainwave activity, including, without limitation, wave frequency, wave amplitude, and waveform type in order to effectively identify one or more characteristics, phases or states of brain activity. In aspects of this embodiment, a neuromodulation device disclosed herein comprises a plurality of EEG electrodes having sufficient sensitivity to detect and measure alpha waves, theta waves, delta waves, sleep spindles, K complexes, or any combination thereof.

Neuromodulation device 110 can comprise a planar, open-curved arc, or closed-curved arc configuration of EEG electrodes. The planar, open-curved arc, or closed-curved arc configuration of EEG electrode is a configuration designed to provide optimal measurement of brainwave activity, including, without limitation, wave frequency, wave amplitude, and waveform type in order to effectively identify one or more characteristics, phases or states of brain activity. In some embodiments, a neuromodulation device disclosed herein is a one-dimensional planar, curved or closed curved arc configuration of EEG electrodes. In some embodiments, each EEG electrode can be controlled in isolation, or in clusters to reduce cabling.

In some embodiments, a neuromodulation device disclosed herein comprises a two-dimensional planar, open-curved arc, or closed-curved arc configuration of EEG electrodes. In aspects of these embodiments, a two-dimensional planar, open-curved arc, or closed-curved arc configuration of a neuromodulation device can comprise, e.g., 2, 3, 4, or 5 rows of EEG electrodes. In other aspects of these embodiments, a two-dimensional planar, curved or closed curved arc configuration of a neuromodulation device can comprise, e.g., at least 2, at least 3, at least 4, or at least 5 rows of EEG electrodes. In yet other aspects of these embodiments, a two-dimensional planar, curved or closed curved arc configuration of a neuromodulation device can comprise, e.g., at most 2, at most 3, at most 4, or at most 5 rows of EEG electrodes. In still other aspects of these embodiments, a two-dimensional planar, curved or closed curved arc configuration of a neuromodulation device can comprise, e.g., 2-3 rows of EEG electrodes, 2-4 rows of EEG electrodes, 2-5 rows of EEG electrodes, 3-4 rows of EEG electrodes, 3-5 rows of EEG electrodes, or 4-5 rows of EEG electrodes.

The number of EEG electrodes comprising a neuromodulation device disclosed herein is a number designed to provide optimal measurement of brainwave activity, including, without limitation, wave frequency, wave amplitude, and waveform type in order to effectively identify one or more characteristics, phases or states of brain activity. In aspects of this embodiment, a neuromodulation device comprises, e.g. 1, 2, 3, 4, 5, 6, 7, 8, 9 or 10 EEG electrodes. In aspects of this embodiment, a neuromodulation device comprises, e.g., at least 1, at least 2, at least 3, at least 4, at least 5, at least 6, at least 7, at least 8, at least 9 or at least 10 EEG electrodes. In yet aspects of this embodiment, a neuromodulation device comprises, e.g., at most 1, at most 2, at most 3, at most 4, at most 5, at most 6, at most 7, at most 8, at most 9 or at most 10 EEG electrodes. In still aspects of this embodiment, a neuromodulation device comprises, e.g., 2-3 EEG electrodes, 2-4 EEG electrodes, 2-5 EEG electrodes, 2-6 EEG electrodes, 2-7 EEG electrodes, 2-8 EEG electrodes, 2-9 EEG electrodes, 2-10 EEG electrodes, 3-4 EEG electrodes, 3-5 EEG electrodes, 3-6 EEG electrodes, 3-7 EEG electrodes, 3-8 EEG electrodes, 3-9 EEG electrodes, 3-10 EEG electrodes, 4-5 EEG electrodes, 4-6 EEG electrodes, 4-7 EEG electrodes, 4-8 EEG electrodes, 4-9 EEG electrodes, 4-10 EEG electrodes, 5-6 EEG electrodes, 5-7 EEG electrodes, 5-8 EEG electrodes, 5-9 EEG electrodes, 5-10 EEG electrodes, 6-7 EEG electrodes, 6-8 EEG electrodes, 6-9 EEG electrodes, 6-10 EEG electrodes, 7-8 EEG electrodes, 7-9 EEG electrodes, 7-10 EEG electrodes, 8-9 EEG electrodes, 8-10 EEG electrodes, or 9-10 EEG electrodes.

In some embodiments, a neuromodulation device disclosed herein contains multiple EEG electrode located on the front portion of the main band positioned at the forehead of a user above the eyebrows and on each side of the main band positioned at the left and right temple region of a user above the ears. In aspects of these embodiments, a neuromodulation device disclosed herein comprises four EEG electrodes, with two EEG electrodes located on the front portion of the main band with one positioned above the left eyebrow of a user and the other positioned above the right eyebrow of the user, one EEG electrode located on the left side of the main band positioned at the left temple region of a user above the ears, and one EEG electrode located on the left side of the main band positioned at the right temple region of a user above the ears. In other aspects of these embodiments, a neuromodulation device disclosed herein comprises six EEG electrodes, with two EEG electrodes located on the front portion of the main band with one positioned above the left eyebrow of a user and the other positioned above the right eyebrow of the user, two EEG electrodes located on the left side of the main band positioned at the left temple region of a user above the ears, and two EEG electrodes located on the left side of the main band positioned at the right temple region of a user above the ears. In yet other aspects of these embodiments, a neuromodulation device disclosed herein comprises eight EEG electrodes, with four EEG electrodes located on the front portion of the main band with two arrays positioned above the left eyebrow of a user and two arrays positioned above the right eyebrow of the user, two EEG electrodes located on the left side of the main band positioned at the left temple region of a user above the ears, and two EEG electrodes located on the left side of the main band positioned at the right temple region of a user above the ears.

In some embodiments, a neuromodulation device disclosed herein contains a single EEG electrode located on the front portion of the main band positioned at the forehead of a user above the eyebrows and a single ultrasound transducer array located on each side of the main band positioned at the left and right temple region of a user above the ears. In some embodiments, a neuromodulation device disclosed herein contains multiple EEG electrodes located on the front portion of the main band positioned at the forehead of a user above the eyebrows and multiple ultrasound transducer array located on each side of the main band positioned at the left and right temple region of a user above the ears. In aspects of these embodiments, a neuromodulation device disclosed herein comprises two EEG electrodes each located on the front portion of the main band with one positioned above the left eyebrow of a user and the other positioned above the right eyebrow of the user, and a single ultrasound transducer array located on each side of the main band positioned at the left and right temple region of a user above the ears. In other aspects of these embodiments, a neuromodulation device disclosed herein comprises two EEG electrodes each located on the front portion of the main band with one positioned above the left eyebrow of a user and the other positioned above the right eyebrow of the user, two ultrasound transducer arrays located on the left side of the main band, and two ultrasound transducer arrays located on the right side of the main band.

In aspects of this embodiment, a neuromodulation device disclosed herein comprises a plurality of EEG electrodes having sufficient sensitivity to detect and measure brainwave frequencies of, e.g., at least 0.1 Hz, at least 0.2 Hz, at least 0.25 Hz, at least 0.3 Hz, at least 0.4 Hz, or at least 0.5 Hz. In other aspects of this embodiment, a neuromodulation device disclosed herein comprises a plurality of EEG electrodes having sufficient sensitivity to detect and measure brainwave frequencies of, e.g., 0.1 Hz to 50 Hz, 0.1 Hz to 60 Hz, 0.1 Hz to 75 Hz, 0.25 Hz to 50 Hz, 0.25 Hz to 60 Hz, 0.25 Hz to 75 Hz, 0.5 Hz to 50 Hz, 0.5 Hz to 60 Hz, or 0.5 Hz to 75 Hz.

In aspects of this embodiment, an EEG monitoring array disclosed herein provides sufficient sensitivity from the EEG electrodes to detect and measure brainwave amplitudes of, e.g., at least 5 µV, at least 25 µV, or at least 50 µV. In other aspects of this embodiment, an EEG monitoring array disclosed herein provides sufficient sensitivity from the EEG electrodes to detect and measure brainwave amplitudes of, e.g., 5 µV to 500 µV, 5 µV to 750 µV, or 5 µV to 1,000 mV, 25 µV to 500 µV, 25 µV to 750 µV, 25 µV to 1,000 mV, 50 µV to 500 µV, 50 µV to 750 µV, or 50 µV to 1,000 mV.

A neuromodulation device disclosed herein is configured to provide spacing between each EEG electrode in order to provide optimal measurement of brainwave activity, including, without limitation, wave frequency, wave amplitude, and waveform type in order to effectively identify one or more characteristics, phases or states of brain activity. In aspects of this embodiment, a neuromodulation device comprises a plurality of EEG electrodes are equally spaced with one another. In aspects of this embodiment, a neuromodulation device comprises a plurality of EEG electrodes where each EEG electrode spaced apart from one another by, e.g., about 20 mm, about 25 mm, about 30 mm, about 35 mm, about 40 mm, about 45 mm, about 50 mm, about 55 mm or about 60 mm. In other aspects of this embodiment, a neuromodulation device comprises a plurality of EEG electrodes where each EEG electrode spaced apart from one another by, e.g., at least 20 mm, at least 25 mm, at least 30 mm, at least 35 mm, at least 40 mm, at least 45 mm, at least 50 mm, at least 55 mm or at least 60 mm. In yet other aspects of this embodiment, a neuromodulation device comprises a plurality of EEG electrodes where each EEG electrode spaced apart from one another by, e.g., at most 20 mm, at most 25 mm, at most 30 mm, at most 35 mm, at most 40 mm, at most 45 mm, at most 50 mm, at most 55 mm or at most 60 mm. In yet other aspects of this embodiment, a neuromodulation device comprises a plurality of EEG electrodes where each EEG electrode spaced apart from one another by, e.g., about 20 mm to about 30 mm, about 20 mm to about 40 mm, about 20 mm to about 50 mm, about 20 mm to about 60 mm, about 30 mm to about 40 mm, about 30 mm to about 50 mm, about 30 mm to about 60 mm, about 40 mm to about 50 mm, about 40 mm to about 60 mm, or about 50 mm to about 60 mm.

A neuromodulation device disclosed herein further contains conductive wiring. Such conductive wiring can be located exteriorly on the device housing or embedded within wearable device housing 120, such as, e.g., within a channel, and will exit the housing through a port located at the back. In some embodiments, the conductive wiring will exit cable port 160 parallel to the cranium in the anterior-posterior direction allowing the user to lay on his back against the flush wires. Conductive wiring disclosed herein powers an EEG amplification stage for each EEG electrode 150, each ultrasound transducer array 140, stimulation control unit 200 and its associated processing elements and functions, and other components of neuromodulation device 110 and can be bundled together. In some embodiment, conductive wiring runs through a channel within main band 122 connecting each EEG electrode 150 to one or more amplifiers, a digital analog converter, and a stimulation control unit 200 before exiting via cable port 160 located at a back portion of main band 122. In some embodiment, and with respect to each ultrasound transducer array 140, conductive wiring runs through a channel within main band 122 connecting each ultrasound transducer array 140 to stimulation control unit 200 before exiting via cable port 160 located at a back portion of main band 122.

Figure 2:
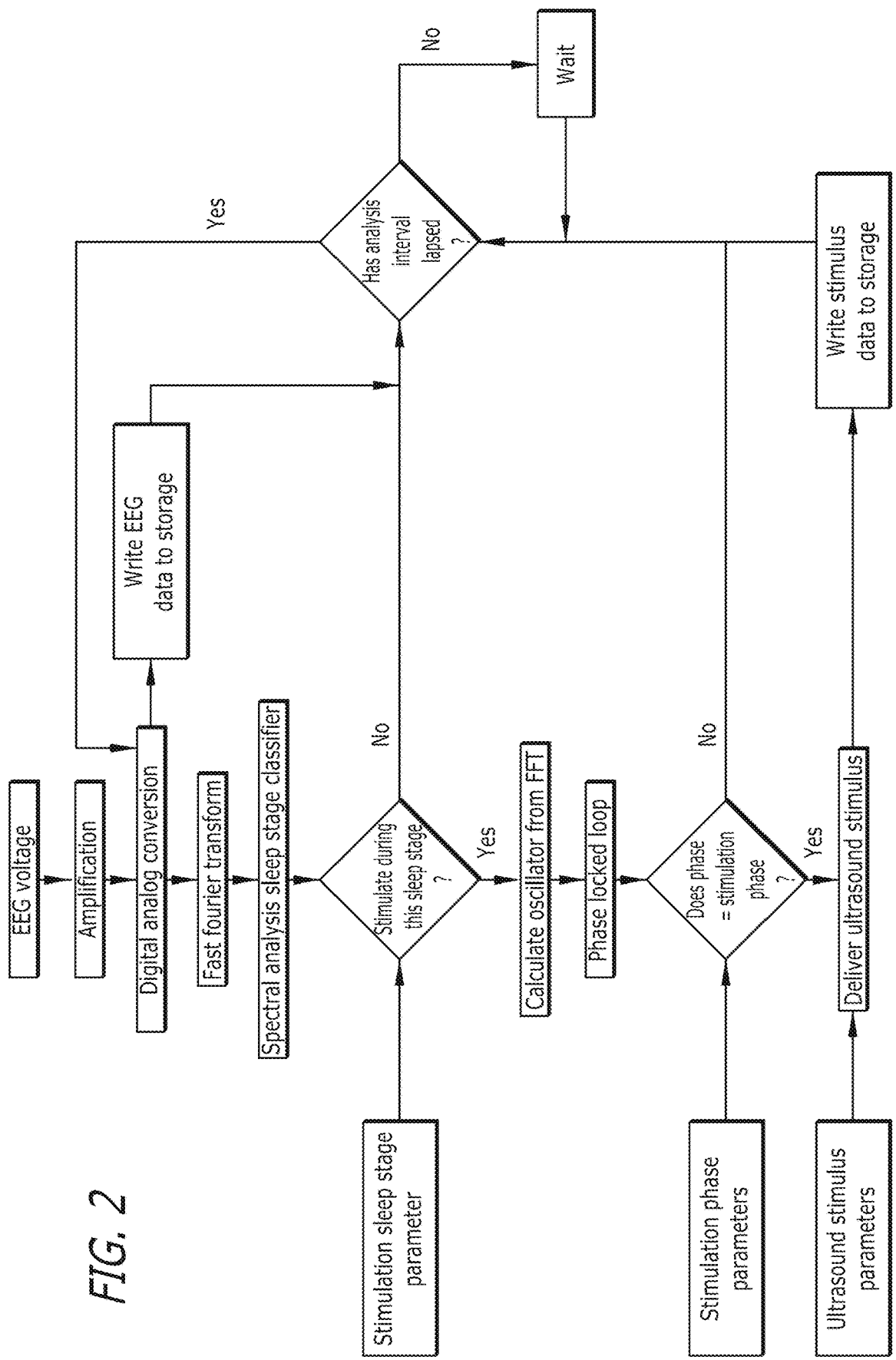
FIG. 2 is a schematic of an exemplary algorithmic framework of a stimulation control unit disclosed herein showing various exemplary aspects and steps of processing EEG signals from a user in real-time and generation of ultrasound stimulus in accordance with the teachings of the instant disclosure.

Aspects of the present specification disclose a neuromodulation system comprising a stimulation control computing environment including a stimulation control unit and an offline computing device. Referring to FIG. 1A, neuromodulation system 100 further contains a stimulation control unit 200 located on main band 122 or tethered to main band 122 with conductive wiring 210 via a cable port 160. Stimulation control unit 200 comprising a central control ASIC processor, a printed circuit board (PCB) component which contains an ultrasound phase control component, one or more signal amplifiers, an ultrasound matching network as well as a power source and other processors. The ASIC chip processes EEG data, ultrasound state data, ultrasound-emitting element target phase data, power usage, and data storage. This ASIC processor sends information regarding element phase which triggers the ultrasound phase control component and one or more signal amplifiers of the PCB component. This PCB component then sends signals to the ultrasound matching network to reduce reflections from acoustic impedance mismatch and then to each ultrasound-emitting element 142 of ultrasound transducer array 140, which allow for beam steering on neuromodulation device 110. The battery unit contained in stimulation control unit 200 is appropriately current and voltage rated for the needs of neuromodulation device 110. Stimulation control unit 200 uses an input file regarding phase delays for each target structure, which can be subdivisions of a single target as well as a stimulation protocol for each target. This file is loaded through a bus interface, such as, e.g., a LIGHTNING connector, a micro-USB connector, a USB-C connector, and the like, and is derived through acoustic simulations performed on a brain image set of the user wearing neuromodulation device 110. The simulation maps patients target brain regions relative to ultrasound-emitting elements 142 of each ultrasound transducer array 140 and appropriately phase corrects each element timing such that a beam focuses on the target. An exemplary algorithmic framework of a stimulation control unit disclosed herein is shown in FIG. 2.

Referring to FIG. 1A, a stimulation control computing environment disclosed herein also comprises an offline computing device 250 comprises an algorithmic framework including one or more processors and a plurality of software and hardware components (including a digital analog converter, function generator, and hard drive) configured to execute program instructions or routines to perform the data processing and performance functions that controls the operability of a neuromodulation device disclosed herein.

An algorithmic framework of stimulation control unit 200 and software elements disclosed herein is part of the one or more systems and methods that apply mathematical functions, models or other analytical and data processing techniques in real-time to ensure a neuromodulation device disclosed herein applies ultrasound stimulation in an appropriate spatial and temporal manner to one or more specific regions of the brain separately and differentially in response to the brain activity data obtained by an EEG electrode. The software elements include an offline element, referred to herein as offline algorithmic mapping element 300, and an online element, referred to herein as online algorithmic stimulation application element 310.

The systems and methods for modulating operation of a neuromodulation device disclosed herein may be implemented in many different computing environments. For example, a permissioned, distributed ledger may be implemented in conjunction with a special purpose computer, a programmed microprocessor or microcontroller and peripheral integrated circuit element(s), an ASIC or other integrated circuit, a digital signal processor, electronic or logic circuitry such as discrete element circuit, a programmable logic device or gate array such as a PLD, PLA, FPGA, PAL, and any comparable means. In general, any means of implementing the methodology illustrated herein can be used to implement the various aspects of the present invention. Exemplary hardware that can be used for the present invention includes computers, handheld devices, telephones (e.g., cellular, Internet enabled, digital, analog, hybrids, and others), and other such hardware. Some of these devices include processors (e.g., a single or multiple microprocessors), memory, nonvolatile storage, input devices, and output devices. Furthermore, alternative software implementations including, but not limited to, distributed processing, parallel processing, or virtual machine processing can also be configured to perform the methods described herein.

The systems and methods for modulating operation of a neuromodulation device disclosed herein may also be partially implemented in software that can be stored on a storage medium, executed on programmed general-purpose computer with the cooperation of a controller and memory, a special purpose computer, a microprocessor, or the like. In these instances, the systems and methods of this invention can be implemented as a program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Figure 3A:
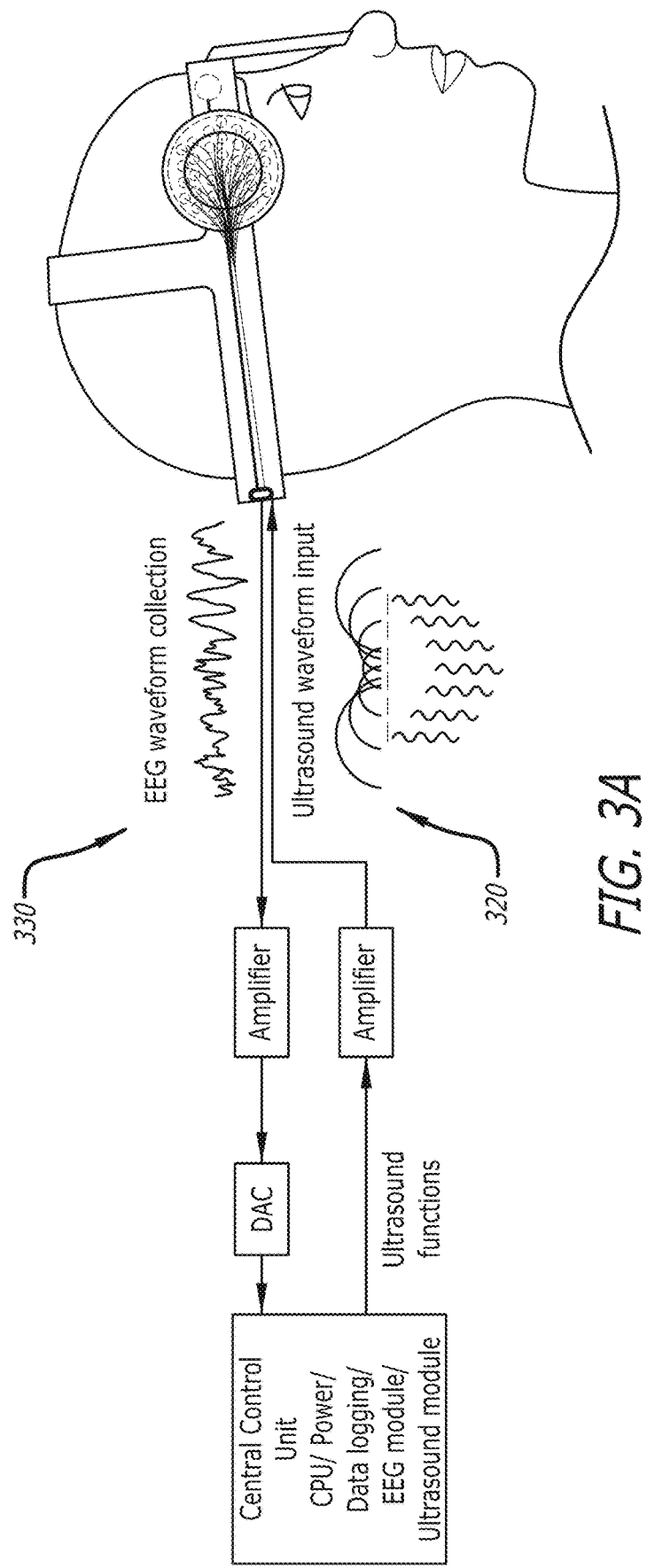
FIGS. 3A-B are exemplary components of a neuromodulation system disclosed herein, with FIG. 3A showing the data collection and modulation systems in accordance with various aspect of the teachings of the present disclosure.
Figure 3B:
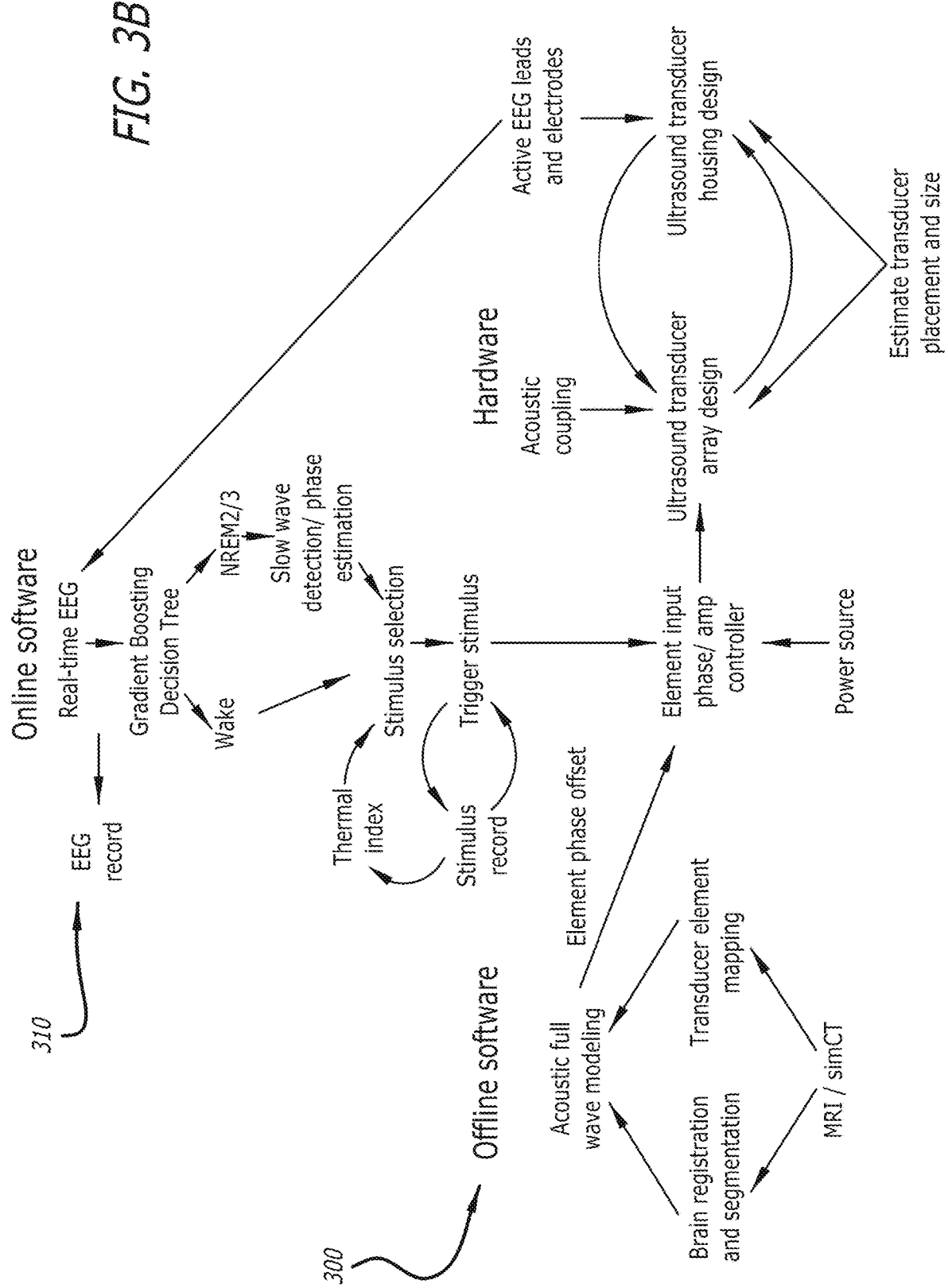
Figure 4A:
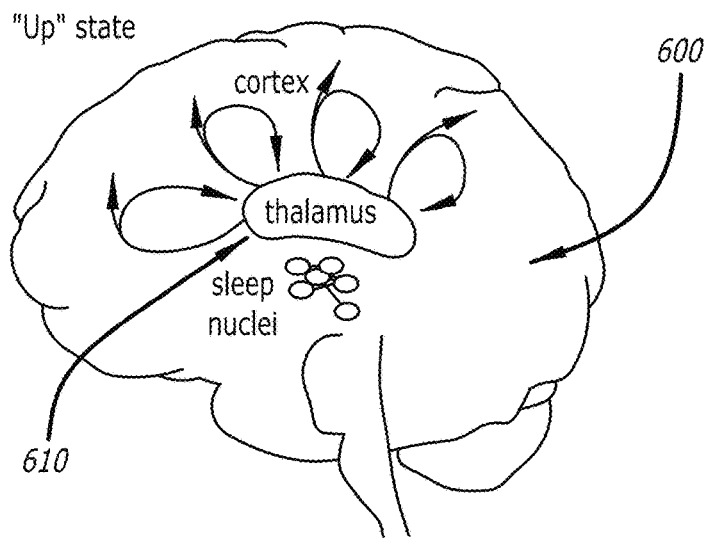
FIGS. 4A-E show exemplary illustrations of network synchronization between the thalamus and cortical layers of the brain, with FIG. 4A showing the thalamic excitatory network interaction with the cortex during slow wave "Up" state.
Figure 4C:
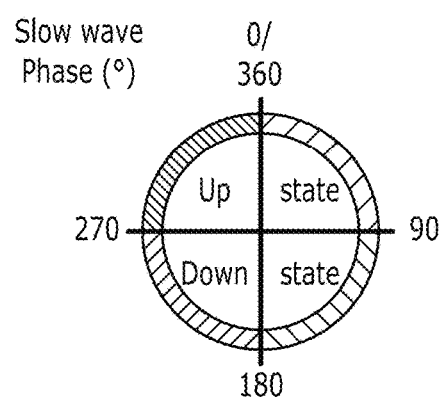
Figure 4B:
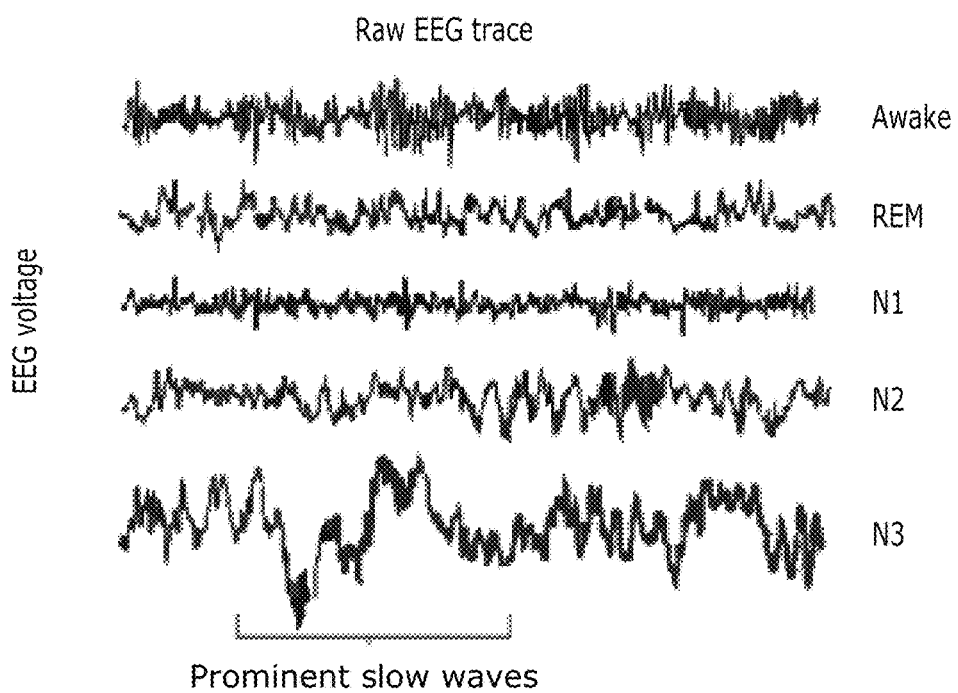
Figure 4D:
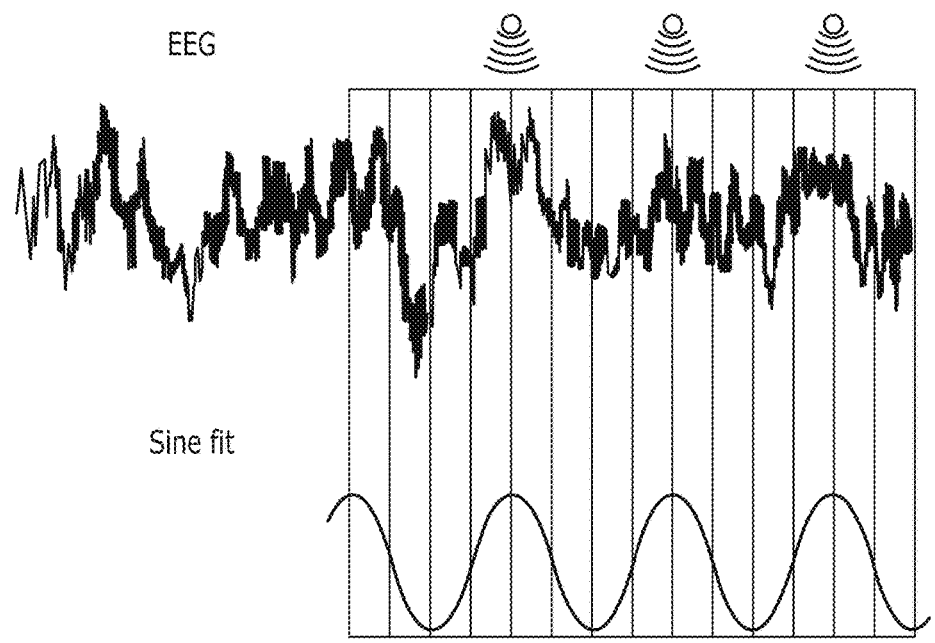
Figure 4E:
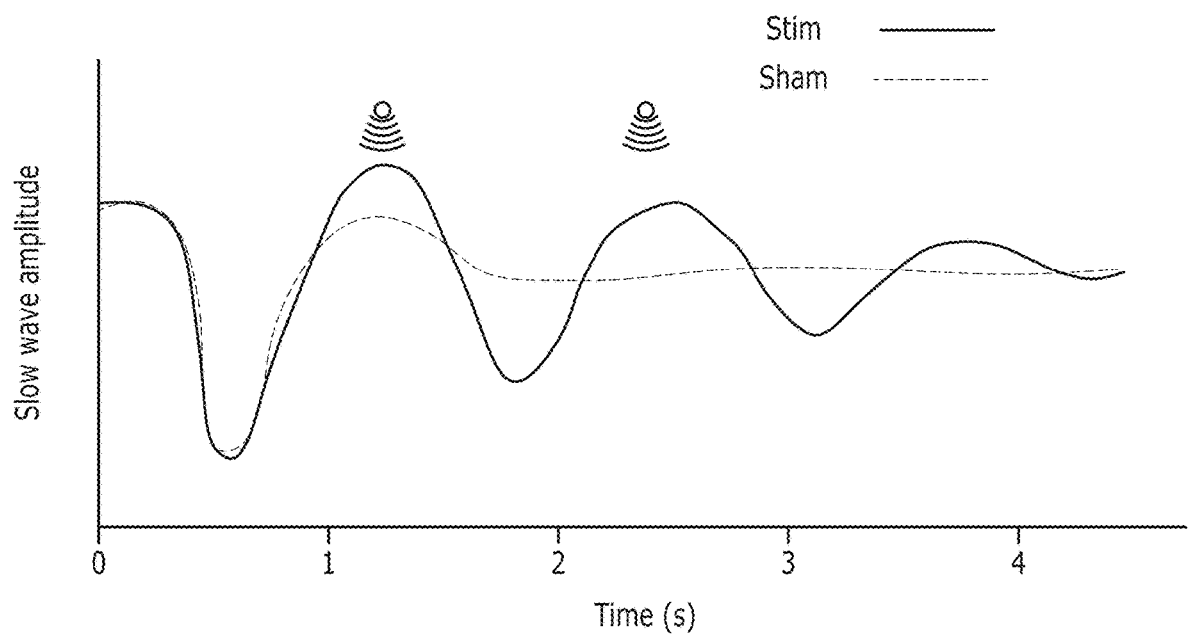

Additionally, the data processing functions disclosed herein may be performed by one or more program instructions stored in or executed by such memory, and further may be performed by one or more modules configured to carry out those program instructions. Modules are intended to refer to any known or later developed hardware, software, firmware, artificial intelligence, fuzzy logic, expert system or combination of hardware and software that is capable of performing the data processing functionality described herein. The device includes three key software modules: the EEG controller module that includes a sleep stage classifier and slow wave analysis functionality, the ultrasound module that controls the ultrasound beamforming and stimulation pattern, and a data logging module that captures all the interaction data for optimization purposes (FIG. 3A-B).

A stimulation control unit disclosed herein has the capacity for temporary and long-term data storage to available hard-drive space. Depending on the memory capacity of a stimulation control unit, data can be down-sampled prior to writing to each file using time-window averaging. Stored data include, without limitation, a timestamp, real-time information received by an EEG electrode disclosed herein, information generated by a stimulation control unit disclosed herein and information received by an ultrasound transducer array disclosed herein.

EEG electrode information includes EEG data for each electrode which is preferably stored as a microvolt time series sampled at 256 Hz. Ultrasound transducer array information includes ultrasound stimulus information which is preferably stored as a 256 Hz binary time series with stimulus delivery status, for example, where 1 reflects that the ultrasound delivery waveform is on, 0 reflects that the ultrasound delivery waveform is off. Voltage waveform pattern delivered to each ultrasound transducer element during stimulation periods is unique to each user and can be stored on a stimulation control unit in a standard format. This file includes contents such as, for example, ultrasound transducer element phase delay, fundamental frequency, burst modulation frequency, and interburst-interval. In some instances, there can be several of these files which create specific focal points in brain space. For instance, one file may produce focusing on the centromedian thalamus, and another the reticular nucleus of the thalamus.

A stimulation control unit can further include one or more systems and methods that apply mathematical functions, models or other analytical and data processing techniques in real-time for battery management, data offloading/onloading, or other operations designed into a neuromodulation device disclosed herein. Regarding user-specific data offloading/onloading, the stimulation control unit can be internet connected and the data storage on each neuromodulation device will be automatically scanned for new data files and offloaded as necessary.

An exemplary system and method for modulating operation of a neuromodulation device disclosed herein is shown in FIG. 3. Brain activity data, including frequency, amplitude, waveform, is continuously being collected by an EEG electrode disclosed herein and the collected data is and amplified. This and amplified brain activity data is then passed from a digital analog conversion (DAC) board and then relayed to one or more processors of a stimulation control unit. The stimulation control unit then executes brain activity software to analyze this EEG information in order to categorize the brain activity and if specified criteria are met, initiate protocols for the administration of ultrasound stimulation. A stimulation control unit disclosed herein then executes phase corrected beam steering based on offline phase instructions generated by an offline algorithmic mapping element 300. These instructions are generated offline using brain image data and brain substructure mapping software that analyzes the cranial anatomy of a user to identify one or more specific region of the brain and accurately identifies the target locations designated for ultrasound stimulation. Phase correction instructions for each element are determined by performing acoustic simulations on brain image data to predict optimal focusing parameters. Once these regions of the brain have been mapped, a stimulation control unit disclosed herein then instructs an ultrasound transducer array disclosed herein to administer ultrasound signal to these mapped brain regions for a certain period of time and with or without signal amplification. Constant input from an EEG electrode disclosed herein results in a continuous initiation and/or adjustment from a stimulation control unit disclosed herein, which regulates the application of ultrasound by an ultrasound transducer array disclosed herein. This results in a feedback mechanism that enables timely, effective, and accurate ultrasound stimulation to one or more specific brain region requiring such stimulation.

Aspects of the present specification disclose, in part, a system and method for processing real-time information acquired an EEG electrode disclosed herein, in an online algorithmic stimulation application element 310. The disclosed system and method for processing this real-time EEG information comprises brain activity analysis software that evaluates the EEG information in order to categorize the brain activity, determines whether the brain activity measured met specified criteria, and if such criteria are satisfied, initiates protocols for the administration of ultrasound stimulation, including brain substructure mapping and ultrasound administration.

In some embodiments, brain activity analysis software evaluates brain activity in order to categorize the sleep stage of a sleep cycle in order to determine slow wave signals indicative of Stage N2 of NREM or Stage N3 of NREM sleep. The device will identify the current phase of slow waves for the proper application of ultrasound stimulus using the algorithm shown in part by FIG. 2. In this application, phase with respect to an EEG measure refers to the point along a cycle or oscillation of a recorded brain region between a positive and negative measured voltage. To identify the present slow wave phase while the device is operational, spectral analysis will be performed on a segment of the most recent acquired EEG signal; this will typically be, but is not limited to, the last 4 seconds of signal acquired. A spectral analysis will be performed on this segment in which the contribution of all brain wave frequencies, also known as the frequency domain, is determined. In an aspect of this embodiment, a spectral analysis is perform using a Fast Fourier Transform (FFT) analysis to determine the frequency domain. The system will then determine the dominant slow wave frequency by determining the maximum contributing frequency between 0.5 Hz and 2 Hz. This dominant slow wave frequency will then be used to determine the current slow wave phase. The signal may be bandpass filtered for the dominant frequency to remove extraneous signals greater than or less than the dominant signal. To determine the phase of the filtered or unfiltered signal several methods can be used. In one embodiment, a sine wave function with the dominant frequency will be fit to the filtered EEG signal. The current slow wave phase will be determined by the ending phase of the sine wave fit to the EEG signal. If the signal acquisition is delayed, the sine wave may be extended beyond the data to predict future phase. In another method a phase locked loop may be used. A phase locked loop is a type of control system which detects the phase difference of a reference signal and an input signal, effectively allowing a system to identify the occurrence of a crest and trough of a wave signal in time. Once phase has been determined through either of these methods, or some other suitable method, the system will then deliver the ultrasound stimulus if the phase meets one or more certain criteria as illustrated in FIGS. 4A-E. This may be that the phase is matched to or within a given number of degrees or radians of the "up state" in which the measured voltage is most positive. This "up state" is generated by the thalamic bursting activity engaging the corticothalamic loop. Alternatively, the criteria may be that the phase matches the "down state" in which the corticothalamic loop is inactive.

Depending on the ultrasound response of the targeted cell type, the relative phase of administration may vary. In aspects of this embodiment, a protocol for administering an ultrasound stimulation is initiated when the phase of a slow wave frequency is, e.g., about 50°, about 55°, about 60°, about 65°, about 70°, about 75°, about 80°, about 85°, about 90°, about 95° from the peak slow wave frequency. In other aspects of this embodiment, a protocol for administering an ultrasound stimulation is initiated when the phase of a slow wave frequency is, e.g., at least 50°, at least 55°, at least 60°, at least 65°, at least 70°, at least 75°, at least 80°, at least 85°, at least 90°, at least 95° from the peak slow wave frequency. In yet other aspects of this embodiment, a protocol for administering an ultrasound stimulation is initiated when the phase of a slow wave frequency is, e.g., at most 50°, at most 55°, at most 60°, at most 65°, at most 70°, at most 75°, at most 80°, at most 85°, at most 90°, at most 95° from the peak slow wave frequency. In still other aspects of this embodiment, a protocol for administering an ultrasound stimulation is initiated the phase of a slow wave frequency is, e.g., about 50° to about 60°, about 50° to about 70°, about 50° to about 80°, about 50° to about 90°, about 50° to about 100°, about 60° to about 70°, about 60° to about 80°, about 60° to about 90°, about 60° to about 100°, about 70° to about 80°, about 70° to about 90°, about 70° to about 100°, about 80° to about 90°, about 80° to about 100°, or about 90° to about 100° from the peak slow wave frequency.

Aspects of the present specification disclose, in part, a system and method for mapping one or more specific regions of the brain. The disclosed system and method for mapping one or more specific regions of the brain comprises brain substructure mapping software that identifies one or more specific region of the brain and accurately plots one or more targeting locations designated for ultrasound stimulation as illustrated in FIGS. 5A-J. Ultrasound focusing of a neuromodulation device disclosed herein relies on the convergence of coordinated interference of acoustic waves from different pressure sources along the ultrasound transducer array, which are affected by non-linearities in skull thickness and brain morphology of a user's cranium as well as by non-linearities in skull incidence angle. In addition, such heterogeneous skull and brain morphology can differ substantially between users. A brain substructure mapping software disclosed herein models optimal ultrasonic focusing parameters catered to each user's unique cranial morphology by identifying these non-linearities and variations and accounting for them when plotting a solution to properly steer ultrasound stimulation of a particular region of the brain.

A brain substructure mapping software disclosed herein identifies one or more specific regions to be targeted for ultrasound stimulation. In some embodiments, one or more specific regions of the brain are identified by comparing a brain image scan to a brain atlas which may be publicly available or internally annotated in order to identify a common coordinate space. Brain image scans include scans generated by computed tomography (CT) and magnetic resonance imaging (MRI). Non-limiting sources of such brain image scans include scans obtained from a user of a neuromodulation device disclosed herein (personalized model customized for a particular user), scans obtained from deidentified individuals through healthcare facilities, or scans obtained from deidentified individuals through registries like the Human Connectome. Brain image scans are registered with a common brain region atlas and image segmentation performed to identify centroids in voxel space of the one or more specific regions to be targeted for ultrasound stimulation. In some embodiments, the target brain region is the thalamus. In some embodiments, the one or more specific regions to be targeted for ultrasound stimulation is a sub-region of the thalamus such as, but not limited to the central nucleus of the thalamus, the reticular thalamus, or the lateral thalamus or some combination thereof.

In some embodiments, one or more specific regions of the brain are identified using biometric parameters that coordinate with brain region. The target site may be estimated as a point in 3D space relative to a biometric which has some predictive value for the position of the target site. This biometric may include, but is not limited to, the position of a person's eyes, ears, eyebrow ridge, nose, mouth, jawline, or other appendage relative to a cranial landmark. This biometric may also include a relative point along a cranial feature axis, such as a fractionally defined mid-point along the forehead, between the ears and eyes, between the corner of the mouth to the base of the ear, or some other combination of cranial features or appendages.

Once the one or more specific brain regions are identified, a brain substructure mapping software disclosed herein identifies the coordinate space of each transducer elements within the image data. It then accurately calculates the temporal phase offset of ultrasound-emitting elements based by estimating acoustic temporal path length between the element and the target of one or more identified locations or performing full wave simulation. Initially the software will determine acoustic impedance by employing an algorithm that converts pixels of a brain image scan from the brain modeling database into measurements of acoustic impedance (Hounsfield units). A brain substructure mapping software disclosed herein then determines the beam steering required to effectively apply ultrasound stimulation onto a given region of the brain. In some embodiments, the required beam steering is determined by modeling simulations of wave equations by estimating the temporal wave path length to the target focus, accounting for difference in sound speed across skull and tissue as well as wave refraction. The simulation then adjusts the excitation phase delay of each ultrasound transducer element until the wave fronts constructively interfere at the focus.

In some embodiments, a model using acoustic simulation software provides 3-D matrices of beam characteristics given certain phase and power inputs applied to the ultrasound transducer elements. This can include the maximum possible power distribution ratio between on and off-target structures in the x, y, and z domain, characteristics of beam deformation at large steering angles, and/or minimum achievable focal sizes. In some embodiments, the target brain site can be determined by iterative stimulation of different locations of a region which should contain the target site. With this method a general target space can be estimated from a brain-skull model database or a focal distribution based on user data as illustrated in FIGS. 5A-J. This space may have probabilistic features where certain layers of 3D coordinate space may be more likely to contain the target site than others. The transducer can be programmed to scan this 3D space in a stepwise fashion while measuring a biological readout. The scanning coordinate space may be evenly spaced, giving equal examination weight to each point, or may be unevenly spaced to reflect the probability that the target site is present at a given coordinate. The coordinate space may be static throughout the examination or may be dynamic to reflect positive or negative biological readouts at each coordinate during the examination. The biological readout may be a feature of EEG such as slow wave amplitude, or a subjective measure described by the user such as a sensory experience or a description of state of mind. The readout may be performed once at each coordinate, multiple times, or a weighted number of times based on the probabilistic space.

In some embodiments, a brain substructure mapping software disclosed herein determines the required beam steering by plotting the maximum lateral steering angles to the edges of the targeted brain region from a fixed reference point on the user's cranium. In aspects of these embodiments, a brain substructure mapping software disclosed herein determines the required beam steering by plotting the maximum angle from the ultrasound transducer array to the maximum and minimum lateral steering angles of the target brain region.

Figures 5A, 5B, 5C, 5D:
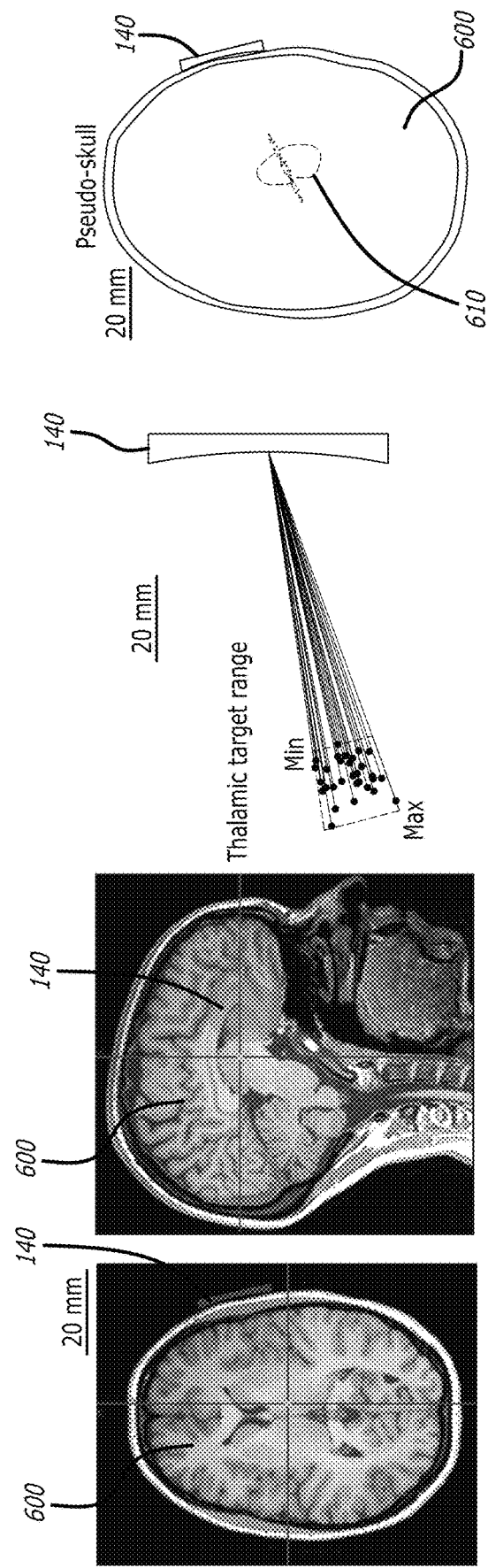
FIGS. 5A-J show an exemplary MRI-based methodology utilized for computational measurements for determining and applying focused ultrasound to a specific targeted neural region during a pre-use calibration step, with FIG. 5A showing an image created by MRI scanning taken from an axial plane with anterior commissure marked as control point (crosshairs) used to compute the maximum angle relative to most posterior and anterior portion of the thalamus.
Figure 5E:
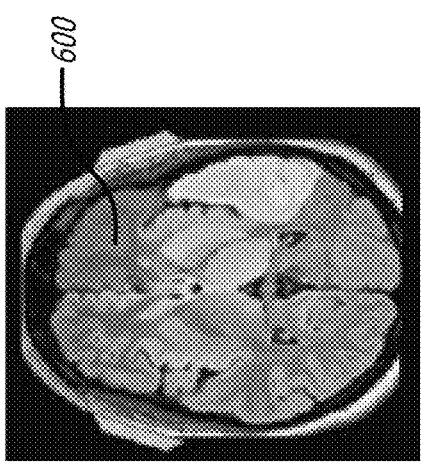
Figure 5F:
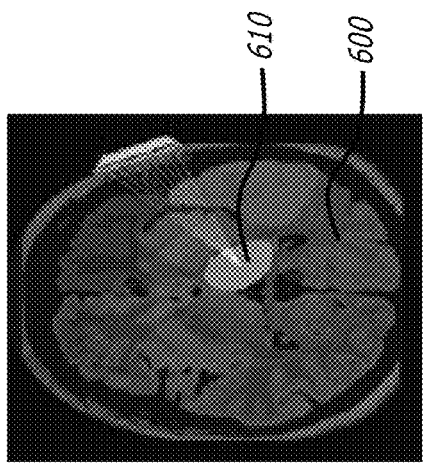
Figure 5G:
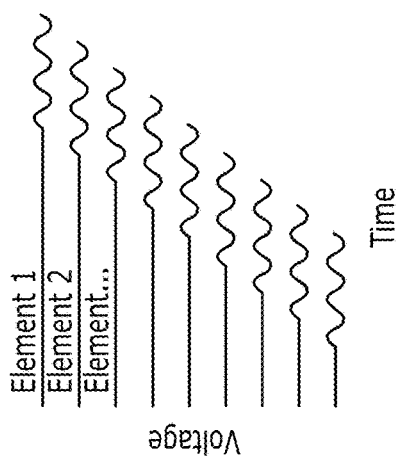
Figure 5H:
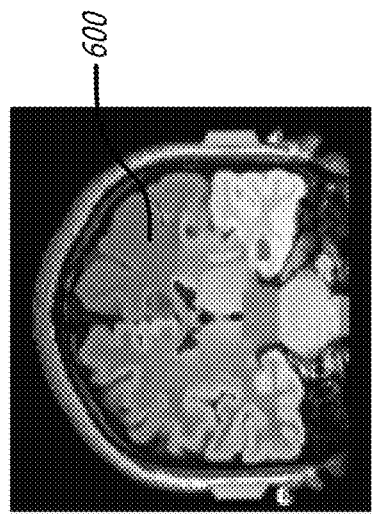
Figure 5I:
Figure 5J:
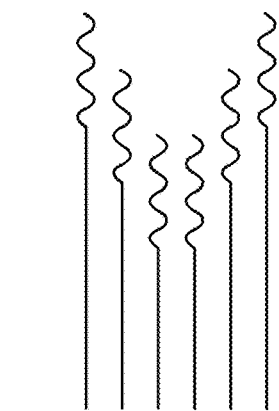

In some embodiments, a brain substructure mapping software disclosed herein maps the location of the thalamus. For example, and as illustrated in FIGS. 5A-B, the location of thalamus 610 is mapped using a brain modeling database and the maximum angle relative to most posterior and anterior portion of the thalamus is computed on a converted MRI scan by marking the anterior commissure as a control point (FIG. 5A, crosshairs) and placement of ultrasound transducer array 140 (FIG. 5B) of neuromodulation device 110 as a set point and the dashed lines indicate focal point steering angles. As illustrated in FIGS. 5C-D, projection of ultrasound stimulation from a neuromodulation device disclosed herein established a pressure field that engages only a portion of the thalamus with the highest intensity part of the field. As another example, and as illustrated in FIGS. 5E & 5H, a brain substructure mapping software disclosed herein maps the location of the thalamus (purple) using a brain modeling database and then, as shown in FIGS. 5F & 5I, accurately plots application of ultrasound stimulation to the thalamus.

In some embodiments, a brain substructure mapping software disclosed herein creates a file format that contains user specific information regarding a targeted brain region, and the necessary phase delay for each ultrasound transducer element.

A stimulation control unit of a neuromodulation device disclosed herein includes an implementation of artificial intelligence, in systems and methods that apply one or more techniques of machine learning for determination of sleep stage, EEG spectral analysis, and controlling ultrasound emitting elements accordingly. The present invention contemplates that many different types of artificial intelligence, and more specifically machine learning may be employed, and are within the scope thereof. The application of artificial intelligence and machine learning may include, in addition or lieu of the neural network, one or more of such types of artificial intelligence. These may include, but are not limited to, techniques such as k-nearest neighbor (KNN), logistic regression, support vector machines or networks (SVM), and instantiations of one or more other types of machine learning paradigms such as supervised learning, unsupervised learning, deep learning and reinforcement learning. Regardless, the use of artificial intelligence and machine learning in the algorithmic framework of the present invention enhances the utility of data processing functions performed therein by automatically and heuristically constructing appropriate relationships, mathematical or otherwise, relative to the complex interactions between data obtained from the plurality of sensors and other input data used by a stimulation control unit, to arrive at the most appropriate response to particular vehicular operating conditions.

Aspects of the present specification also disclose a stimulation control unit comprising machine learning elements such as a deep learning model for sleep stage prediction. Such an application of artificial intelligence systems in the present invention involves automatically monitoring, classifying, quantifying EEG information to predict the sleep stages of a user in real time. A deep learning model for sleep stage prediction will first use representation learning to extract useful features from the raw EEG data using convolutional neural networks (CNN) to detect features on the raw data, such as, e.g., using 1D convolutions on the raw EEG or 2D convolutions on the Spectrograms. A deep learning model for sleep stage prediction will then employ sequence residual learning by using recurrent and fully connected cell layers to classify the features extracted from the first part into sleep stages. The use of recurrent cells allows the temporal dimension to be considered in the problem. A deep learning model for sleep stage prediction will also include an error correction layer that will deal with movement artifacts and other external noises by using an encoder-decoder approach.

Figure 7A:
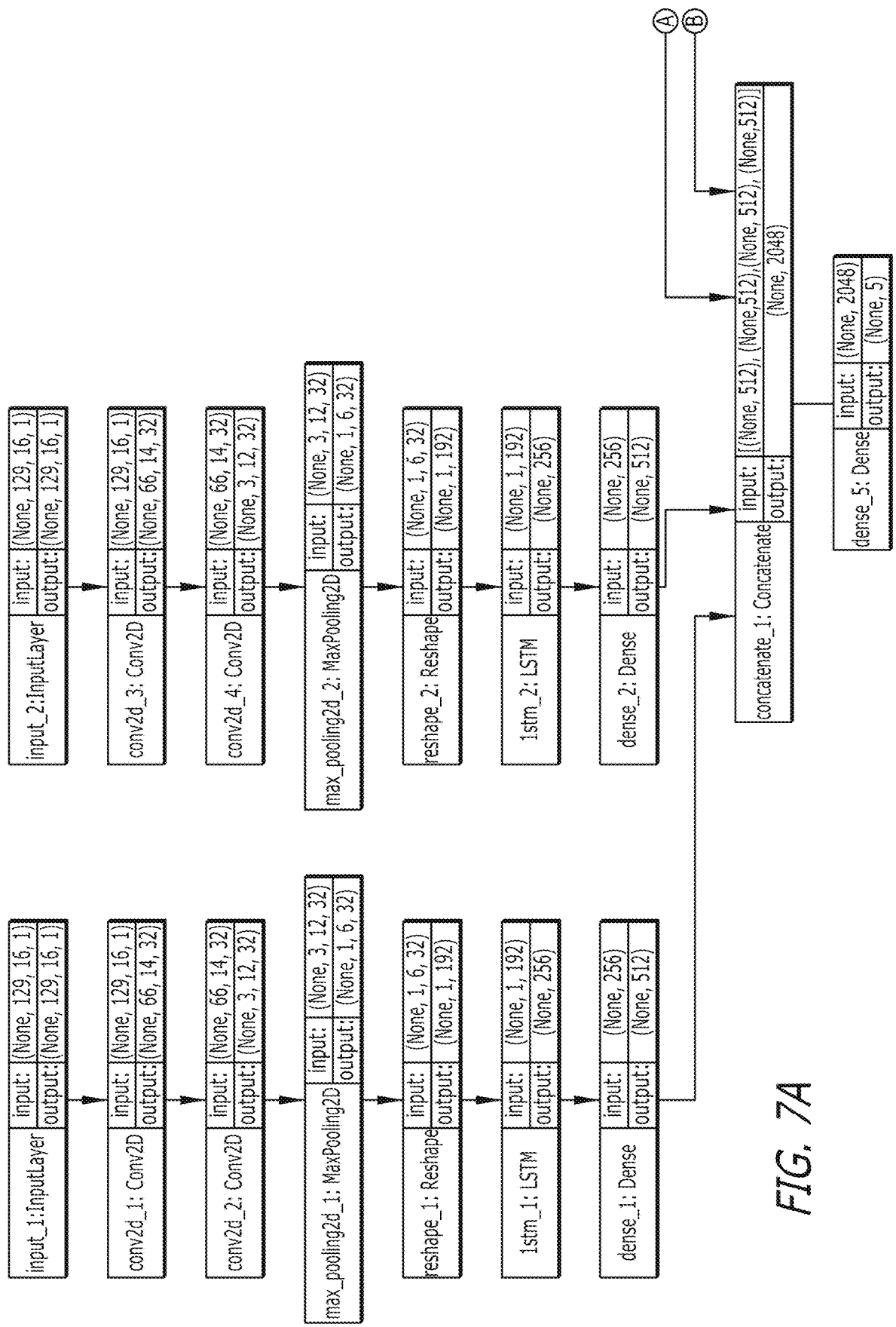
FIGS. 7A-B show a schematic of an exemplary control system algorithm for enhancing slow waves, with FIG. 7A showing one portion of the exemplary control system algorithm.
Figure 7B:
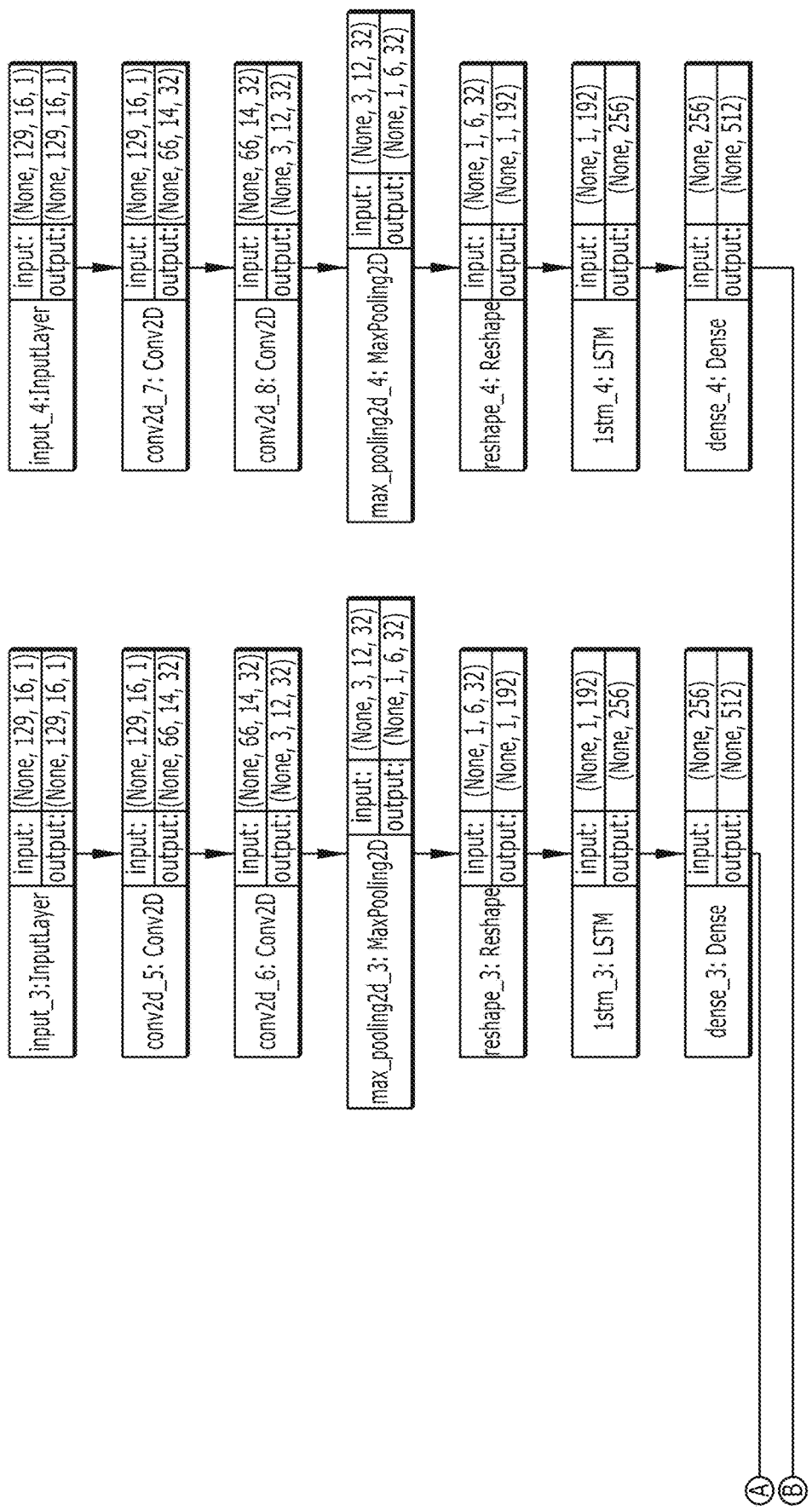

In some embodiments, and as shown in FIGS. 7A-B, a deep learning model for sleep stage prediction comprises one multi-branch that uses four signal (EEG, EOG-R, EOG-L, and EMG) input architecture. The multi-branch deep learning model for sleep stage prediction is composed by four branches of convolutional neural networks and a LSTM. The tensors are concatenated at the end of the branches and fed into a fully connected layer. This last fully connected layer can be fine-tuned to allow personalization with transfer learning. A bidirectional LSTM that will be used as a baseline for evaluating the single EEG signal architecture.

Figure 8A:
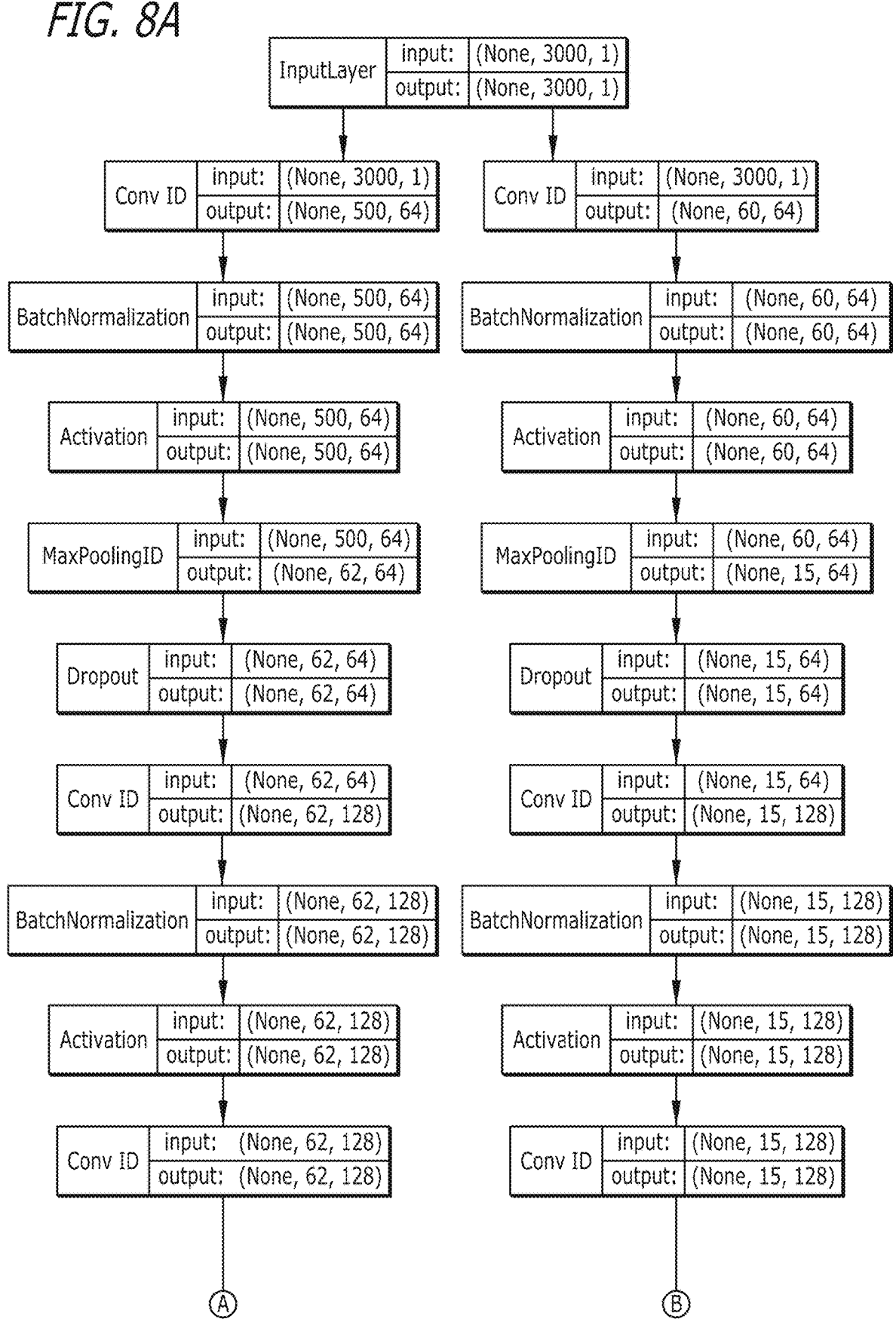
FIGS. 8A-C show a schematic showing an exemplary deep learning network for multi-signal input, with FIG. 8A showing a first portion of the exemplary deep learning network.
Figure 8B:
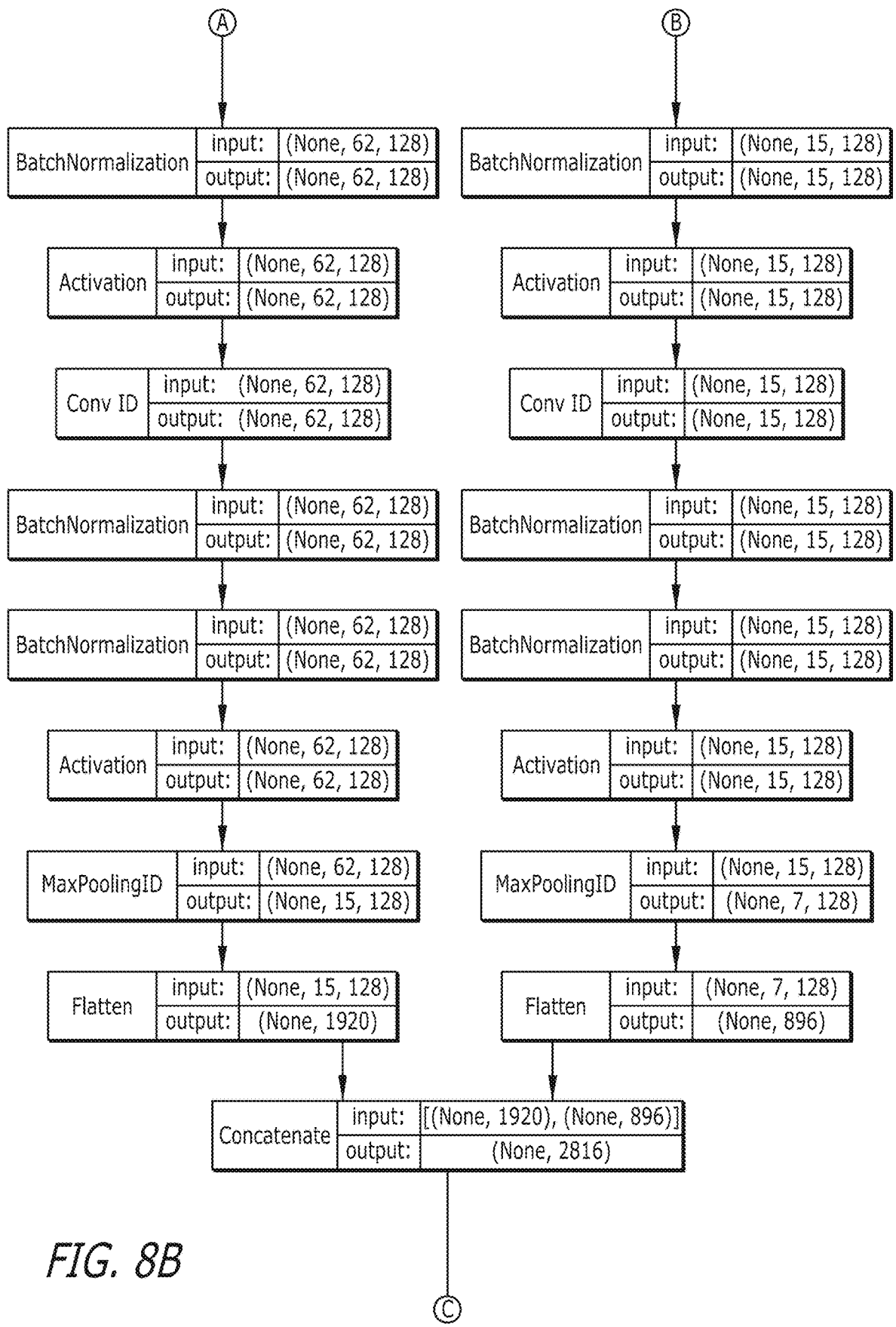
Figure 8C:
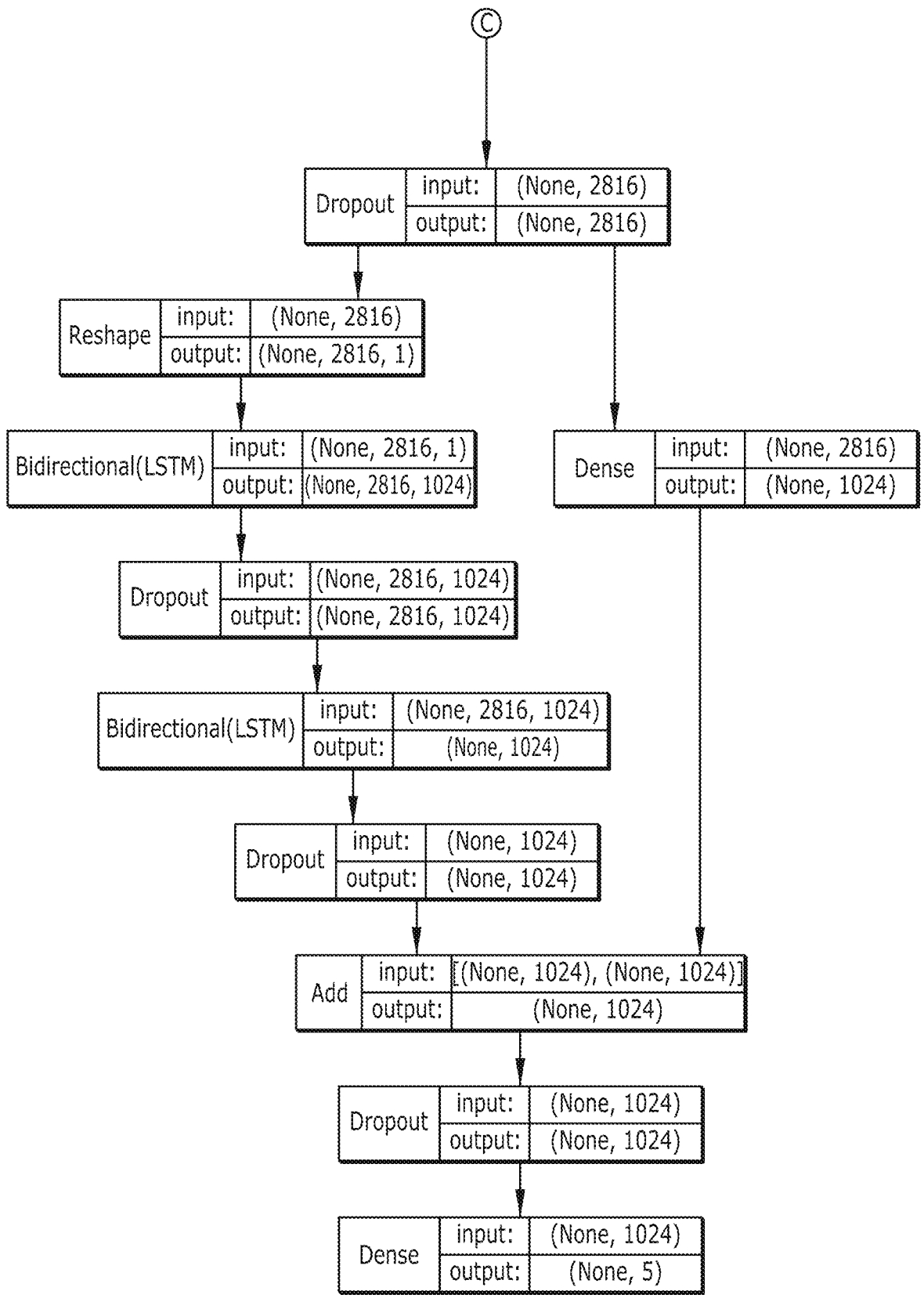

In some embodiments, and as shown in FIGS. 8A-C, a deep learning model for sleep stage prediction comprises one or two branches that use a single signal (EEG) input architecture. Each branch of a one or two branch deep learning model for sleep stage prediction is a convolutional neural network with different filter configurations to capture different features from the signal. Those tensors are concatenated and then fed to another two branches one with a bidirectional long short-term memory and one with a fully connected layer. The results are concatenated again and fed to a final fully connected layer.

In some embodiments, a deep learning model for sleep stage prediction is based on bidirectional recurrent networks with large short-term memory and trained with thousands of labelled polysomnograms. Such a deep learning model for sleep stage prediction enables classification of polysomnogram and EEG in real time to allow for personalization of the classification to a given user. In aspects of these embodiments, a deep learning model for sleep stage prediction is based on bidirectional recurrent neural network (RNN) with or without long short-term memory (LSTM).

In some embodiments, a deep learning model for sleep stage prediction is developed by creating a database of whole night polysomnograms based on publicly available information. Such polysomnograms can be obtained from healthy individuals as well as from individuals suffering from a relevant sleep condition, such as, e.g., drug-resistant insomnia, REM sleep behavior disorder, or narcolepsy.

In some embodiments, a deep learning model for sleep stage prediction is developed by creating a personalized database of whole night polysomnograms from the same individual. Such polysomnograms can be obtained by having a user sleep under controlled conditions and manually labeling them in order to refine the last layers weights by retraining them for a few epochs. A personalized database is useful to retrain the last layer of the deep learning model in order to adapt to the differences of each individual, allowing a neuromodulation device disclosed herein to be personalize to the user.

Aspects of the present specification also disclose a stimulation control unit comprising a deep learning model for regulating ultrasound stimulation parameters. Such an application of artificial intelligence systems involves automatically determining and adjusting in real time the ultrasound stimulation parameters required for modulating brain activity. A deep learning model for regulating ultrasound stimulation parameters can read information from the deep brain at an individualized level, and in real time instruct a neuromodulation device disclosed herein to deliver the required ultrasound stimulation to achieve its desired outcome. In some embodiments, the deep learning model automatically determines and adjusts in real time the ultrasound stimulation parameters required for modulating brain activity in order to improve sleep quality of sleep. In some embodiments, a deep learning model for regulating ultrasound stimulation parameters comprises 1) reinforcement learning to adapt in real time to changes in the device position and other external factors; 2) subsystem routines that control an EEG electrode; and 3) a data logging module used for training long-term personalization and for improving the other modules.

In some embodiments, a neuromodulation device disclosed herein targets the thalamus with focused ultrasound stimulation as shown in FIG. 5A-I. Despite having no direct interaction with the cortex, focused ultrasound stimulation of the thalamus ultimately engages greater volumes of cortex through the corticothalamic loop. The corticothalamic loop is a circular network of neurons involving connections between the cortex, the basal ganglia, the thalamus, and back to the cortex. The two major pathways of the loop are the striatum and the subthalamic nucleus (STN). The striatum receives excitatory inputs from the cortex and modulatory inputs from the pars compacta of the substantia nigra (SNc), while the subthalamic nucleus only receives excitatory inputs from the cortex. Two pathways emerge from the striatum. One pathway is called the indirect (or NoGo) pathway that projects to and inhibits the globus pallidus externus (GPe), resulting in the disinhibition of the globus pallidus internus (GPi), leading to inhibition of the thalamus. This pathway also, as a result of inhibiting the GPe, disinhibits the subthalamic nucleus, which results in excitation of the GPi, and therefore inhibition of the thalamus. The second pathway, is called the direct (or Go) pathway that projects to and inhibits the GPi, resulting in the disinhibition of the thalamus. Disinhibition of the thalamus results in neuronal stimulation of the cortex while inhibition of the thalamus prevents such stimulation. The corticothalamic loop receives inputs from subthalamic regions encoding bodily homeostasis, as well as peripheral sensory information, such as touch and sound. Its projections spread vastly into cortex as well as other sleep and wake promoting regions, where information oscillates between structures, creating a spatially broad network of information flow.

A neuromodulation device disclosed herein is positioned by placing the device housing on the user's head and adjusting the main and secondary bands to locate the EEG electrodes in the appropriate locations, such as e.g., the forehead and left and right temple regions as well as the ultrasound transducer arrays in the appropriate locations, such as e.g., the left and right temporal window regions. After the device housing is properly adjusted, the position of a neuromodulation device disclosed herein is securely fixed to ensure proper operation.

Figure 6:
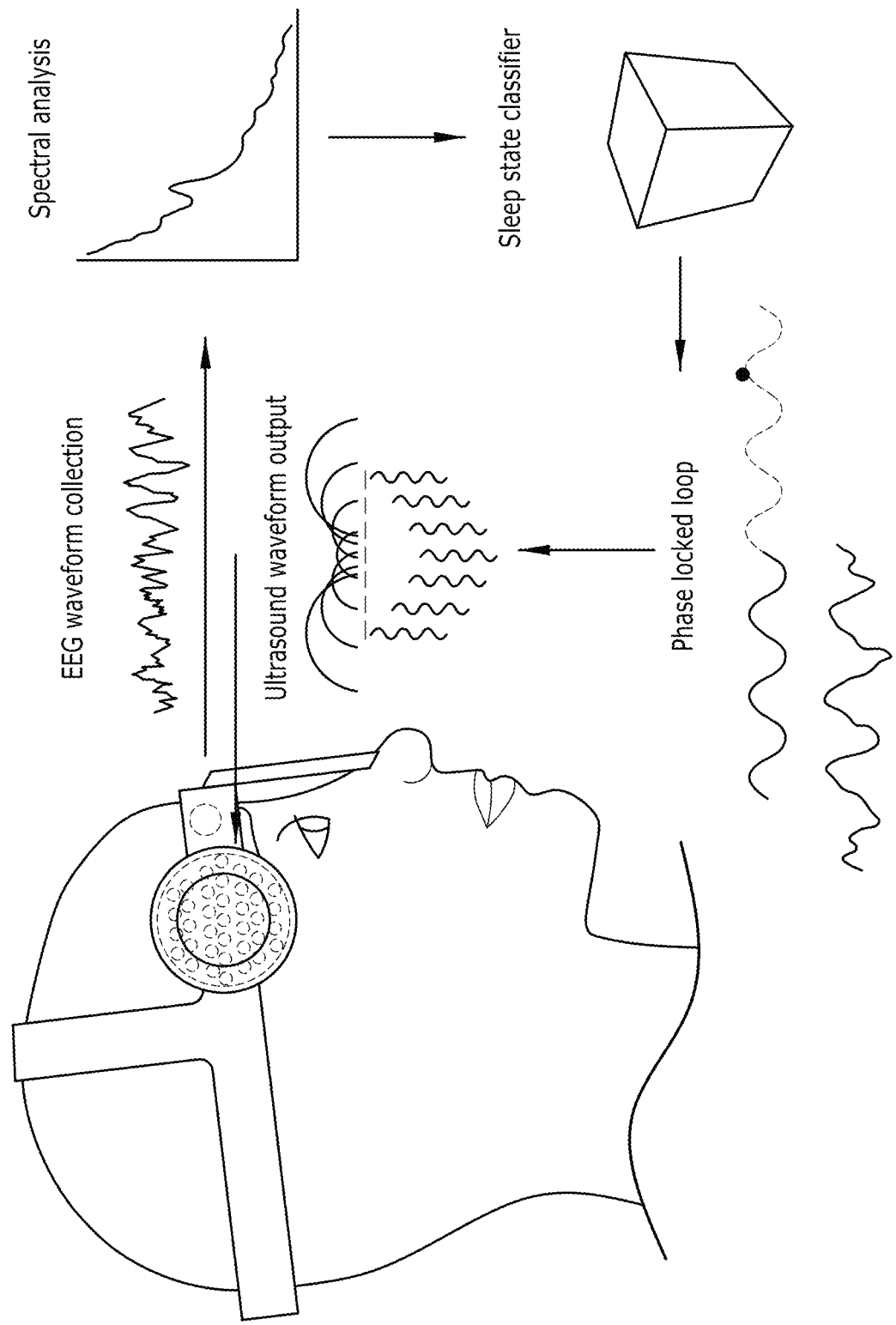
FIG. 6 is an illustration of exemplary components of a device and system of the instant disclosure, showing the closed-loop optimization based on EEG waveform collection, spectral analysis, sleep state classifier and phase lock loop in accordance with various aspect of the teachings of the present disclosure.

In operation, and as shown in FIG. 6, a neuromodulation device disclosed herein continually measures and processes real-time EEG signals from a user's brain to instantaneously identify the current sleep stage of the user. In some embodiments, sleep stage is determined using the ratio of distinct spectral components such as delta (0.5-4 Hz), theta (4-8 Hz), alpha (8-12 Hz) and beta (12-30 Hz) power. When the device categorizes a sleep stage as N2 of NREM or Stage N3 of NREM, the brain activity software of a device disclosed herein will then determine the dominant frequency of the FFT within the slow wave frequency range which will be used as an oscillator for determining the slow wave phase using a phase locked loop. If the phase locked loop finds the slow waves within a given phase range relative to the peak slow wave frequency, the transducer beam steering parameters targeting the thalamus will, apply focused ultrasound stimulation to the thalamus, increasing thalamic activity, thereby enhancing SWS.

Depending on the prescribed operation of the device, the ultrasonic waveforms can specifically be delivered during NREM stages of sleep, or alternatively, can be delivered during wake state. If the sleep stage is assigned stimulation, the device finds the peak spectral component of the FFT. A phase locked loop algorithm is applied to generate a phase locked signal to the real signal (reference signal) to determine the current phase of the slow wave. If the current phase is within the stimulus range, the ultrasound stimulus is triggered for the duration of the inter-packet interval. Once the inter-packet interval has elapsed, the routine is initiated again continuously while the device is set to operate.

Aside from the implementation described above, a neuromodulation device disclosed herein can be used to examine optimal spatial parameters of ultrasound stimulation. The device examines a baseline delta power and compares it to delta power changes achieved with different focal points in a space, as well as different slow-wave phase of ultrasound delivery. The space points can be confined to space surrounding the thalamus, or to the maximal steering capacity of the transducer.

During wear the neuromodulation device is powered on via a single button on the device. EEG is acquired and analyzed at 120 Hz. The central process control unit uses a gradient boosted decision tree algorithm to determine sleep stage and identify slow waves in real time. If the user is in Stage N2 or N3 of NREM and is experiencing a slow wave, the neuromodulation device sends a single continuous 100 ms pulse of focused ultrasound energy to the thalamus in order to enhance thalamic activity and, in turn, the amplitude of the slow wave and subsequent slow waves. Depending on the thalamus width, the device may raster scan the beam over the structure throughout the duration of the stimulation. A time out period is then set which must lapse until subsequent stimulations; this ensures tissue heating is limited to less than 1° C. Throughout wear, EEG time series data and ultrasound stimulation state time series are stored on the central processing unit and offloaded onto an external computing device using a bus interface, such as, e.g., a LIGHTNING connector, a micro-USB connector, a USB-C connector, and the like.

The present specification also discloses methods and uses for preventing and/or treating a brain disorder using a neuromodulation device disclosed herein. Non-limiting aspects of a brain disorder include a sleep disorder of a brain disorder associated with a sleep disturbance, a psychiatric disorder, a metabolic disorder, an epilepsy or other seizure disorder, an anxiety, a depression, and/or a neuropathic pain.

A neuromodulation device disclosed herein could be used to prevent or treat a sleep disorder or disorders associated with a sleep disturbance which arise from or could be remedied by sites in the deep brain. This could include but is not limited to modulating activity of the thalamus or thalamic subregions for enhancement of slow wave sleep or sleep spindle generation for enhancing memory, immune function, cognitive function, and general restorative sleep functionality.

A neuromodulation device disclosed herein could be used to prevent or treat a psychiatric disorder which arise from or could be remedied by sites in the deep brain. This could include but is not limited to modulating activity of the thalamus or thalamic subregions for enhancement of slow wave sleep or sleep spindle generation for enhancing memory, immune function, cognitive function, and general restorative sleep functionality.

A neuromodulation device disclosed herein could be used to prevent or treat a metabolic disorder which arise from or could be remedied by sites in the deep brain. This could also include modulating activity of the locus coeruleus for increasing or decreasing wakefulness. This could also include modulating activity of the hypocretin/orexin neurons of the lateral hypothalamus for modulating wakefulness, emotional state, or appetite. This could include modulating activity of the hypothalamus or hypothalamic sub regions for treating metabolic disorders, increasing or decreasing metabolism, modifying appetite, or thermoregulation.

A neuromodulation device disclosed herein could be used to prevent or treat an epilepsy or seizure disorder which arise from or could be remedied by sites in the deep brain. This could also include modulating activity of the thalamus or thalamic subregions for treating focal and non-focal seizures or temporal lobe epilepsy.

A neuromodulation device disclosed herein could be used to prevent or treat a depression or anxiety which arise from or could be remedied by sites in the deep brain. This could also include modulating activity of the amygdala for treating and/or altering emotional states such as depression or anxiety.

The present specification also discloses methods and uses for promoting healthy brain aging and prevent age related brain diseases using a neuromodulation device disclosed herein. Such age-related brain diseases could be due to accumulation of toxic debris and impaired metabolism, stroke and neurodegenerative diseases.

The present specification also discloses methods and uses for preventing and treating jetlag, for inducing hibernation for preventing body damage (e.g. after surgery or after trauma), space travels and for improving cognitive performance for specific requirements such as those mental requirements made of pilots, soldiers, executives and students taking exams, for example.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the devices, or methods and systems disclosed herein.

Example 1

Deep Learning Model for Sleep Stage Prediction

A database comprising whole night polysomnograms was created from three publicly available data Sets representing over 6,700 individual polysomnograms. From this compiled database, 153 polysomnograms were extracted from healthy individuals the Pz-OZ channel of the EEG data was preprocessed with 4th-order Butterworth band-pass filters centered at delta, theta, alpha and beta spectrum (1-4 Hz, 4-8 Hz, 8-13 Hz, 13-30 Hz respectively). From the resulting four signals, for every epoch, four temporal features were extracted: median amplitude, variance, skewness and kurtosis; and four spectral features were extracted: spectral edge frequency difference, spectral decrease, spectral slope and spectral spread. The resulting 32 features were concatenated from the previous epoch to include causality in the system and making a 64-feature vector representing each epoch. Spectral domain was obtained by means of fast Fourier transform and epochs with movement were removed from the dataset. Finally, the features were normalized. Table 1 shows the different sleep stages in this data set, that was split with 70% for training and 30% for testing.

TABLE 1

Epochs for Processed Sample Data Set

| Subset | Wake | N1 | N2 | N3 | REM |
| --- | --- | --- | --- | --- | --- |
| Training | 198,812 | 15,097 | 47,920 | 9,075 | 17,982 |
| Testing | 85,023 | 6,372 | 20,713 | 3,916 | 7,785 |

Figure 9A:
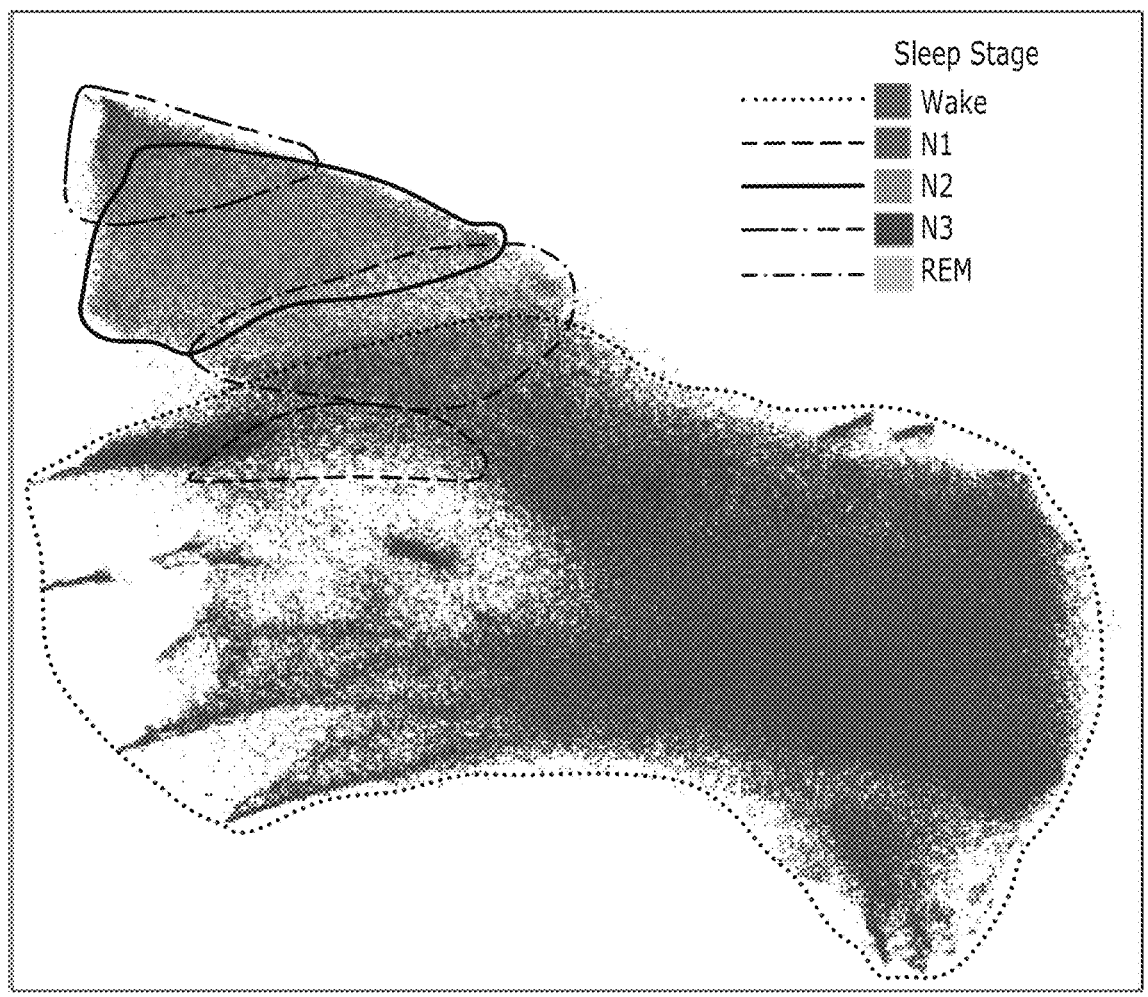
FIGS. 9A-B show results from an exemplary deep learning model for sleep stage prediction, with FIG. 9A showing a two-dimensional plot of the different sleep classes using dimensionality reduction.
Figure 9B:
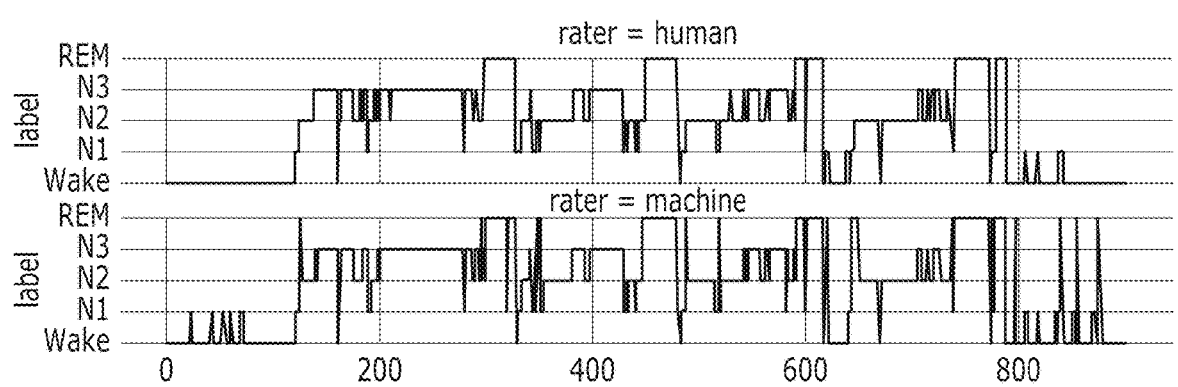

Classification accuracy was tested using several deep learning architectures including CNN, RNN as well as non-linear machine learning algorithms such as random forest or gradient boosting decision trees (GBDT). Using a weighted GBDT model (100 trees) an accuracy of 88% was achieved for all classes, suffering a decrease in accuracy for the less common events (N1 and to a lesser extent in N3, see Table 2). Using a UMAP non-linear dimensionality reduction in two virtual dimensions we can visualize the different classes in FIG. 9A and the quality of the prediction in FIG. 9B.

TABLE 2

Prediction Results for a GBDT Model

| Sleep stage | Precision | Recall | F1-score |
| --- | --- | --- | --- |
| Wake | 0.95 | 0.98 | 0.97 |
| N1 | 0.47 | 0.12 | 0.19 |
| N2 | 0.74 | 0.85 | 0.79 |
| N3 | 0.70 | 0.50 | 0.58 |
| REM | 0.67 | 0.63 | 0.65 |

Example 2

Sleep Study

In this study, participants will wear a neuromodulation device disclosed herein for two consecutive nights' sleep at the clinic. The neuromodulation device will be powered on and set with a file steering data for the individual. On night one optimal spatial peak pulse average intensity ultrasound power will be assessed. The neuromodulation device will emit 200 ms continuous ultrasound waves during the Stage N2 and/or Stage N3 of NREM of sleep, phase locked to the participants slow waves. The minimum inter stimulus delay will be set to 5 seconds in order to allow assessment of slow wave power subsequent to the stimulation. The following intensities will be randomly delivered for each event: 5 $W/cm^2$, 10 $W/cm^2$, 20 $W/cm^2$, and 40 $W/cm^2$ at the 300-360° phase. The ratio of delta power in the 4.7 seconds post stimulation will be assessed relative to the average delta power across all events. During a 7-day period prior to the 2nd study night the optimal power will be examined. The second night of the study will be used to examine optimal stimulation slow wave phase with the given power. The phases of stimulation to be tested are 300-60°, 0-60°, 60-120°, 120-180°, 180-240°, and 240-300° relative to the down state or minimal voltage. The slow wave enhancement will be determined by relative slow wave amplitude following each stimulation parameter set and will be averaged across events. The lowest power dose which achieves statistically indistinguishable slow wave enhancement from higher power levels, and the phase with greatest enhancement will be used.

Example 3

Sleep Study in Individuals Having PTSD Associated with a Sleep Disturbance

In this study, participants diagnosed with PTSD will be designed as a 7-day randomized, double blind, sham controlled study with an adaptive design. Participants will be randomized to either therapy or sham stimulation with a ratio 2:1. Participants will be asked to keep sleep medications unaltered the week before and during the study. The sham intervention will be wearing an operational neuromodulation device set to deliver 0 $mW/cm^2$ ultrasound intensity. The baseline visit will include two-nights of sleep in the sleep lab for adaptation and recording the PSG for defining the sleep architecture of the participants. All participants will be asked to wear the device for 7 nights. The neuromodulation device will be operationally set by a technician to blind the physician to the treatment groups. Treatment will go from 9 pm to 7 am with either the optimal spatial peak pulse average intensity power and phase ultrasound stimulation defined in Example 2 or sham intervention. During each day, between 9 am and 5 pm, participants will be evaluated for performance tests including the effects of the neuromodulation device use on sleep quality and well-being in PTSD. In addition, vital signs, physical examination and sleep habits will be recorded.

Example 4

Sleep Study in Individuals with a Sleep Disturbance

In this study, participants will be randomized to receive either pre-sleep disorder, post-sleep disorder, or sham stimulation. Participants will be instructed to maintain their chronic sleep schedule reported at screening over 7 nights of an "at-home" sleep monitoring phase for 7 nights. They will be encouraged to obtain the optimal 8 hours per night of sleep, with the 8-hour period falling between the hours of 9 pm and 8 am. for 7 days prior to the laboratory phase of the study. The participants' sleep-wake activity will be assessed using actigraphy to ensure adherence to this requirement. Participants will be required to refrain from taking daytime naps or study-prohibited substances during this period. Participants will arrive at the laboratory at approximately 7 pm on the day following the last night of the at-home sleep monitoring phase. Participants will have 10 hours in bed with lights out and will leave the lab after 7 am. Participants will be instructed not to nap during the day and will be monitored throughout this phase with actigraphy. During each night, participants will undergo polysomnographic monitoring. Participants will remain in the lab the day after their last sleep satiation phase night, prior to their night of sleep restriction with treatment. Baseline daytime performance assessment will take place every 4 hrs during each day. This assessment will include a PVT, a math test, and a sleep propensity test. Prior to bedtime on the sleep restriction night, the neuromodulation device will be worn by both stim and sham groups. By 11 pm (+/−10 minutes), participants will be in bed with lights out. The stim group will receive power identified in Example 2, with the neuromodulation device operating as described in the Example 3. The participants in Sham group will sleep for approximately 4 hours without stimulation. Participants who experience less than a total of approximately 90 minutes of sleep during that 4-hour period, will be excluded from further involvement in the study. Additionally, those participants who have not fallen asleep within approximately 75 minutes of lights off (bedtime) will be excluded from further involvement in the study. Stimulation will be immediately terminated if it is causing a subject discomfort and study participation will be terminated at that time; those individuals will be allowed to sleep the rest of the night and be discharged from the study the following morning. The four-hour period of sleep restriction will be followed by a 44-hour period of sleep deprivation, during which performance, mood and sleep propensity will be periodically assessed.

During the first sleep recovery night participants will be asked to wear the neuromodulation device throughout the night. The neuromodulation device will deliver ultrasound for the post-sleep disturbance group. All participants will have two nights of recovery sleep consisting of 8 hours in bed 11 pm to 7 am. Performance assessments will occur periodically on each day following the recovery nights. During the recovery nights, sleep will be objectively monitored using actigraphy and polysomnography. Participants will be dismissed by a study medical investigator by 7 pm or earlier if all planned study procedures and medical clearances are complete on the day after the second recovery night.

In closing, foregoing descriptions of embodiments of the present invention have been presented for the purposes of illustration and description. It is to be understood that, although aspects of the present invention are highlighted by referring to specific embodiments, one skilled in the art will readily appreciate that these described embodiments are only illustrative of the principles comprising the present invention. As such, the specific embodiments are not intended to be exhaustive or to limit the invention to the precise forms disclosed. Therefore, it should be understood that embodiments of the disclosed subject matter are in no way limited to a particular element, compound, composition, component, article, apparatus, methodology, use, protocol, step, and/or limitation described herein, unless expressly stated as such.

In addition, groupings of alternative embodiments, elements, steps and/or limitations of the present invention are not to be construed as limitations. Each such grouping may be referred to and claimed individually or in any combination with other groupings disclosed herein. It is anticipated that one or more alternative embodiments, elements, steps and/or limitations of a grouping may be included in, or deleted from, the grouping for reasons of convenience and/or patentability. When any such inclusion or deletion occurs, the specification is deemed to contain the grouping as modified, thus fulfilling the written description of all Markush groups used in the appended claims.

Furthermore, those of ordinary skill in the art will recognize that certain changes, modifications, permutations, alterations, additions, subtractions and sub-combinations thereof can be made in accordance with the teachings herein without departing from the spirit of the present invention. Furthermore, it is intended that the following appended claims and claims hereafter introduced are interpreted to include all such changes, modifications, permutations, alterations, additions, subtractions and sub-combinations as are within their true spirit and scope. Accordingly, the scope of the present invention is not to be limited to that precisely as shown and described by this specification.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

The words, language, and terminology used in this specification is for the purpose of describing particular embodiments, elements, steps and/or limitations only and is not intended to limit the scope of the present invention, which is defined solely by the claims. In addition, such words, language, and terminology are to be understood not only in the sense of their commonly defined meanings, but to include by special definition in this specification structure, material or acts beyond the scope of the commonly defined meanings. Thus, if an element, step or limitation can be understood in the context of this specification as including more than one meaning, then its use in a claim must be understood as being generic to all possible meanings supported by the specification and by the word itself.

The definitions and meanings of the elements, steps or limitations recited in a claim set forth below are, therefore, defined in this specification to include not only the combination of elements, steps or limitations which are literally set forth, but all equivalent structure, material or acts for performing substantially the same function in substantially the same way to obtain substantially the same result. In this sense it is therefore contemplated that an equivalent substitution of two or more elements, steps or limitations may be made for any one of the elements, steps or limitations in a claim set forth below or that a single element, step or limitation may be substituted for two or more elements, steps or limitations in such a claim. Although elements, steps or limitations may be described above as acting in certain combinations and even initially claimed as such, it is to be expressly understood that one or more elements, steps or limitations from a claimed combination can in some cases be excised from the combination and that the claimed combination may be directed to a sub-combination or variation of a sub-combination. As such, notwithstanding the fact that the elements, steps and/or limitations of a claim are set forth below in a certain combination, it must be expressly understood that the invention includes other combinations of fewer, more or different elements, steps and/or limitations, which are disclosed in above even when not initially claimed in such combinations. Furthermore, insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. Accordingly, the claims are thus to be understood to include what is specifically illustrated and described above, what is conceptually equivalent, what can be obviously substituted and also what essentially incorporates the essential idea of the invention.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including," "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement, and support for the phrases "consisting essentially of" and "consisting of."

Lastly, all patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

The invention claimed is:

1. A neuromodulation system comprising:
a neuromodulation device including a wearable device housing, one or more EEG electrodes for analyzing brain function in real time, one or more EEG signal amplifiers coupled to the one or more EEG electrodes, and one or more ultrasound-emitting elements; and
a stimulation control computing environment comprising a stimulation control unit and an offline computing device, the stimulation control unit comprising at least one processor coupled to the one or more ultrasound-emitting elements, and configured with one or more data processing functions to focus ultrasound emission to a centromedian thalamus, the one or more data processing functions including:
an offline algorithmic mapping element configured to:
use brain image data to identify the centromedian thalamus, and
perform one or more acoustic simulations to determine information for use in focusing ultrasound emissions from the one or more ultrasound-emitting elements to the centromedian thalamus, and
an online algorithmic stimulation application element configured to:
process real-time data acquired by the one or more EEG electrodes to detect a phase of at least one slow wave, and
control the ultrasound emissions from the one or more ultrasound-emitting elements, in accordance with the waveform parameters determined by the offline algorithmic mapping element, such that the ultrasound emissions constructively interfere at the centromedian thalamus to form a plurality of ultrasound pulses focused on the centromedian thalamus during a certain slow wave phase range for enhancing the at least one slow wave based on the detected phase of the at least one slow wave thereby improving a quality of sleep by the user during a sleep stage, wherein the ultrasound emissions are phase locked to the at least one slow wave such that the ultrasound pulses have a frequency in a range below 2 Hertz.

2. The neuromodulation system according to claim 1, wherein the one or more EEG electrodes detects and measures alpha waves, theta waves, delta waves, sleep spindles, K complexes, or any combination thereof.

3. The neuromodulation system according to claim 1, wherein one or more EEG electrodes have a sensitivity to detect and measure at least 0.1 Hz.

4. The neuromodulation system according to claim 1, wherein the one or more ultrasound-emitting elements include at least 64 ultrasound-emitting elements.

5. The neuromodulation system according to claim 1, wherein real-time information processed by the stimulation control unit includes brainwave power spectral distribution and brainwave spectral amplitude to identify the sleep stage.

6. The neuromodulation system according to claim 1, wherein the stimulation control unit adjusts power of the one or more ultrasound-emitting elements based on estimated acoustic attenuation processed from cranial anatomy and/or bone density.

7. The neuromodulation system according to claim 1, wherein the stimulation control unit is configured to determine acoustic impedance and a beam steering parameter using ultrasound generated data and to target the centromedian thalamus with the ultrasound emissions from the one or more ultrasound-emitting elements based on the acoustic impedance and the beam steering parameter.

8. The neuromodulation system according to claim 7, wherein the beam steering parameter determination optimizes a power distribution ratio between a point relative to one or more target regions and off-target regions across different steering angles of the one or more ultrasound-emitting elements.

9. The neuromodulation system according to claim 1, wherein the stimulation control unit controls the one or more ultrasound-emitting elements to deliver the ultrasound emissions during the sleep stage.

10. The neuromodulation system according to claim 9, wherein the stimulation control unit classifies the sleep stage using a gradient boosted decision tree machine learning algorithm.

11. The neuromodulation system according to claim 1, wherein the stimulation control unit further comprises a deep learning model for sleep stage prediction and a deep learning model for regulating ultrasound emissions.

12. The neuromodulation system according to claim 1, wherein the stimulation control unit optimizes the ultrasound emissions based on a current slow wave amplitude reading relative to a baseline slow wave amplitude reading.

13. A neuromodulation system comprising:
a neuromodulation device including a wearable device housing, one or more EEG electrodes for analyzing brain function in real time, one or more EEG signal amplifiers coupled to the one or more EEG electrodes, and one or more ultrasound-emitting elements; and
at least one processor coupled to the one or more ultrasound-emitting elements, the at least one processor configured to control waveform parameters of ultrasound emissions from the one or more ultrasound-emitting elements such that (1) the ultrasound emissions constructively interfere at a centromedian thalamus of a user to form a plurality of ultrasound pulses focused on the centromedian thalamus for a specified period of time and (2) the ultrasound emissions are phase locked to at least one slow wave of the user such that the ultrasound pulses have a frequency that fluctuates in a range below 2 Hertz, the at least one processor configured to process real-time data acquired by the one or more EEG electrodes to detect a phase of the at least one slow wave, the at least one processor further configured to control a timing of the ultrasound emissions based on the detected phase of the at least one slow wave such that each of the ultrasound pulses is focused on the centromedian thalamus during a certain phase range of the at least one slow wave at the centromedian thalamus for enhancing the at least one slow wave thereby improving a quality of sleep by the user during a sleep stage, wherein the at least one processor is further configured to identify the sleep stage based on the real-time data acquired by the one or more EEG electrodes and to control the one or more ultrasound-emitting elements to deliver the ultrasound emissions to the centromedian thalamus in response to identification of the sleep stage by the at least one processor.

14. The system of claim 13, wherein the at least one processor is configured to control the timing of the ultrasound emissions based on the detected phase of the at least one slow wave such that cells of the centromedian thalamus are excited by the ultrasound emissions during an up state of the at least one slow wave.

15. The system of claim 14, wherein the at least one processor is configured to control the one or more ultrasound-emitting elements to focus a single one of the ultrasound pulses to the centromedian thalamus during the up state.

* * * * *